United States Patent
Boyer et al.

(10) Patent No.: US 12,042,307 B2
(45) Date of Patent: Jul. 23, 2024

(54) CONTEXTUAL PATIENT DATA REPRESENTATION AND DISPLAY

(71) Applicant: Covidien LP, Mansfield, MA (US)

(72) Inventors: Robert T. Boyer, Longmont, CO (US);
Yaniv Refaelovich, Givatayim (IL);
David A. Fox, Longmont, CO (US);
Boris Ilin, Rishon-LeZion (IL)

(73) Assignee: COVIDIEN LP, Mansfield, MA (US)

( * ) Notice: Subject to any disclaimer, the term of this patent is extended or adjusted under 35 U.S.C. 154(b) by 1183 days.

(21) Appl. No.: 16/206,518

(22) Filed: Nov. 30, 2018

(65) Prior Publication Data

US 2020/0170582 A1    Jun. 4, 2020

(51) Int. Cl.
| | |
|---|---|
| *G16H 20/60* | (2018.01) |
| *A61B 5/00* | (2006.01) |
| *G16H 10/60* | (2018.01) |
| *G16H 40/63* | (2018.01) |
| *G16H 50/30* | (2018.01) |
| *A61B 5/1455* | (2006.01) |

(52) U.S. Cl.
CPC ............ *A61B 5/746* (2013.01); *A61B 5/7225* (2013.01); *A61B 5/7275* (2013.01); *A61B 5/7425* (2013.01); *A61B 5/743* (2013.01); *A61B 5/7435* (2013.01); *G16H 10/60* (2018.01); *G16H 40/63* (2018.01); *G16H 50/30* (2018.01); *A61B 5/14551* (2013.01)

(58) Field of Classification Search
CPC ........ G16H 40/63; G16H 40/67; G16H 15/00; G16Z 99/00; A61B 5/0031; A61B 5/742; A61B 5/031

USPC .............................................. 705/2; 600/300
See application file for complete search history.

(56) References Cited

U.S. PATENT DOCUMENTS

| | | | |
|---|---|---|---|
| 6,675,044 B2 * | 1/2004 | Chen .................... | A61B 5/0031 607/30 |
| 9,636,070 B2 * | 5/2017 | Kassem ................. | A61B 5/031 |
| 10,095,838 B2 * | 10/2018 | Hebler .................... | G16Z 99/00 |
| 10,636,523 B2 * | 4/2020 | Stocker ................. | G16H 40/63 |
| 10,702,174 B2 * | 7/2020 | Fasciano ................ | A61B 5/742 |
| 2008/0243548 A1 * | 10/2008 | Cafer ..................... | G16H 40/67 705/3 |
| 2011/0004071 A1 * | 1/2011 | Faiola .................... | G16H 15/00 600/300 |

OTHER PUBLICATIONS

Google patents search, Mar. 16, 2022 (Year: 2022).*

(Continued)

*Primary Examiner* — Dilek B Cobanoglu
(74) *Attorney, Agent, or Firm* — Fletcher Yoder, P.C.

(57) ABSTRACT

Methods, systems, and devices for patient monitoring are described. The method may include receiving data related to a physiological parameter of a patient. The method may further include displaying information related to the physiological parameter of the patient in order to indicate how the patient is trending. In some cases, the method may include adjusting the received data and determining a subset of the adjusted values to display at a computing device. In some other cases, the method may include displaying a health indicator based on the health record of the patient on the computing device. The position of the health indicator may be based on a medical relationship between the data indicated by the health indicator and the physiological parameter.

11 Claims, 14 Drawing Sheets

(56) References Cited

OTHER PUBLICATIONS

Optimal filter bandwidth for pulse oximetry, Cite as: Rev. Sci. Instrum. 83, 104708 (2012); https://doi.org/10.1063/1.4759491 Submitted: Jul. 26, 2012•Accepted: Oct. 2, 2012 •Published Online: Oct. 26, 2012, Norbert Stuban and Masatsugu Niwayama, Reviewofscientific Instruments83, 104708 (2012) (Year: 2012).*

* cited by examiner

CONTEXTUAL PATIENT DATA REPRESENTATION AND DISPLAY

BACKGROUND

The following relates generally to patient monitoring, and more specifically to contextual patient representation and display.

In a healthcare facility such as a hospital, physiological parameters of the patient (e.g., heart rate, respiratory rate, blood pressure) may be monitored by one or more medical devices. The medical devices may be battery powered and may transmit (wirelessly or via a wired connection) measured patient data to a computing device such as a bedside monitor or a central nurse station or on any web enabled device connected to the network (e.g., smartphone or tablet).

The measured patient data (e.g., physiological data) may be presented on a display of the computing device. A user (e.g., a doctor, nurse, or other healthcare provider) may view the display in order to determine how the patient is trending (e.g., the health status of the patient over time). In some cases, the data displayed at the computing device may not provide sufficient context to the user. That is, the data may be too noisy, overly simplified, or lacking in context such as patient health record data). As such, users may not analyze the displayed data correctly or efficiently. The lack of accuracy and/or efficiency may lead to delayed or inappropriate responses that could put the patient at risk.

SUMMARY

The described features generally relate to methods, systems, devices, or apparatuses, that support contextual patient data representation and display. A computing device may receive measured physiological data relating to the health of a patient. The computing device may display simplified data corresponding to the measured physiological data, where the simplified data provides relevant context to a health care provider while eliminating noise. The data may be simplified by one or more of filtering the measured physiological data, adjusting the measured physiological data, and rounding the data to a nearest demarcation point. In some cases, the demarcation points may correspond to known standard deviations for the physiological data (e.g., according to the demographic information of the patient). The computing device may display a subset of the simplified data. The data may be displayed as a line graph, where each data point is organized temporally and connected to the neighboring data points via a line. The computing device may also display one or more icons in order to provide contextual information related to the health record of the patient. The icons may provide a visual indicator of certain data related to the patient's health record.

A method of patient monitoring is described. The method may include determining, at a monitor of a patient, a health indicator for visually representing data related to a health record of the patient, receiving, after determining the health indicator, current data corresponding to a monitored physiological parameter, displaying, at a first location on a screen of the monitor, the current data corresponding to the monitored physiological parameter, determining whether there is a medical relationship between the monitored physiological parameter and the health indicator, and displaying the health indicator at a second location on the screen, where a relationship between the first location and the second location is based on the medical relationship between the monitored physiological parameter and the health indicator.

An apparatus for patient monitoring is described. The apparatus may include a processor, memory in electronic communication with the processor, and instructions stored in the memory. The instructions may be executable by the processor to cause the apparatus to determine, at a monitor of a patient, a health indicator for visually representing data related to a health record of the patient, receive, after determining the health indicator, current data corresponding to a monitored physiological parameter, display, at a first location on a screen of the monitor, the current data corresponding to the monitored physiological parameter, determine whether there is a medical relationship between the monitored physiological parameter and the health indicator, and display the health indicator at a second location on the screen, where a relationship between the first location and the second location is based on the medical relationship between the monitored physiological parameter and the health indicator.

Another apparatus for patient monitoring is described. The apparatus may include means for determining, at a monitor of a patient, a health indicator for visually representing data related to a health record of the patient, receiving, after determining the health indicator, current data corresponding to a monitored physiological parameter, displaying, at a first location on a screen of the monitor, the current data corresponding to the monitored physiological parameter, determining whether there is a medical relationship between the monitored physiological parameter and the health indicator, and displaying the health indicator at a second location on the screen, where a relationship between the first location and the second location is based on the medical relationship between the monitored physiological parameter and the health indicator.

A non-transitory computer-readable medium storing code for patient monitoring is described. The code may include instructions executable by a processor to determine, at a monitor of a patient, a health indicator for visually representing data related to a health record of the patient, receive, after determining the health indicator, current data corresponding to a monitored physiological parameter, display, at a first location on a screen of the monitor, the current data corresponding to the monitored physiological parameter, determine whether there is a medical relationship between the monitored physiological parameter and the health indicator, and display the health indicator at a second location on the screen, where a relationship between the first location and the second location is based on the medical relationship between the monitored physiological parameter and the health indicator.

Some examples of the method, apparatuses, and non-transitory computer-readable medium described herein may further include operations, features, means, or instructions for determining that the medical relationship between the monitored physiological parameter and the health indicator may be a causal relationship, where the data represented by the health indicator affects the monitored physiological parameter of the patient, and arranging the first location on the screen and the second location on the screen within a threshold distance based on the causal relationship.

Some examples of the method, apparatuses, and non-transitory computer-readable medium described herein may further include operations, features, means, or instructions for determining that data indicated by the health indicator may be medically unrelated to the monitored physiological parameter of the patient, and arranging the first location on the screen and the second location on the screen above a threshold distance.

In some examples of the method, apparatuses, and non-transitory computer-readable medium described herein, the data represented by the health indicator corresponds to a patient condition, a risk factor for the patient, a current medication of the patient, or a combination thereof.

Some examples of the method, apparatuses, and non-transitory computer-readable medium described herein may further include operations, features, means, or instructions for displaying the current data corresponding to the monitored physiological parameter on a separate page from the health indicator.

In sonic examples of the method, apparatuses, and non-transitory computer-readable medium described herein, the health indicator includes an icon indicating the data related to the health record of the patient and a suggested health action based on the data related to the health record.

Some examples of the method, apparatuses, and non-transitory computer-readable medium described herein may further include operations, features, means, or instructions for filtering the health indicator and one or more additional health indicators by a category to display a subset of the health indicator and the one or more additional health indicators on the monitor.

A method of patient monitoring is described. The method may include determining an expected value for a physiological parameter of a patient based on a health record of the patient, receiving, over a period of time, a set of measured values of the physiological parameter, the set of measured values based on monitoring the physiological parameter of the patient, determining statistical information corresponding to the set of measured values over the period of time, adjusting the set of measured values to a set of adjusted values based on the determined statistical information, determining a set of display values by selecting a subset of the set of adjusted values, the set of display values representing the set of measured values, and displaying a graphical representation of the set of display values in relation to the expected value of the physiological parameter.

An apparatus for patient monitoring is described. The apparatus may include a processor, memory in electronic communication with the processor, and instructions stored in the memory. The instructions may be executable by the processor to cause the apparatus to determine an expected value for a physiological parameter of a patient based on a health record of the patient, receive, over a period of time, a set of measured values of the physiological parameter, the set of measured values based on monitoring the physiological parameter of the patient, determine statistical information corresponding to the set of measured values over the period of time, adjust the set of measured values to a set of adjusted values based on the determined statistical information, determine a set of display values by selecting a subset of the set of adjusted values, the set of display values representing the set of measured values, and display a graphical representation of the set of display values in relation to the expected value of the physiological parameter.

Another apparatus for patient monitoring is described. The apparatus may include means for determining an expected value for a physiological parameter of a patient based on a health record of the patient, receiving, over a period of time, a set of measured values of the physiological parameter, the set of measured values based on monitoring the physiological parameter of the patient, determining statistical information corresponding to the set of measured values over the period of time, adjusting the set of measured values to a set of adjusted values based on the determined statistical information, determining a set of display values by selecting a subset of the set of adjusted values, the set of display values representing the set of measured values, and displaying a graphical representation of the set of display values in relation to the expected value of the physiological parameter.

A non-transitory computer-readable medium storing code for patient monitoring is described. The code may include instructions executable by a processor to determine an expected value for a physiological parameter of a patient based on a health record of the patient, receive, over a period of time, a set of measured values of the physiological parameter, the set of measured values based on monitoring the physiological parameter of the patient, determine statistical information corresponding to the set of measured values over the period of time, adjust the set of measured values to a set of adjusted values based on the determined statistical information, determine a set of display values by selecting a subset of the set of adjusted values, the set of display values representing the set of measured values, and display a graphical representation of the set of display values in relation to the expected value of the physiological parameter.

In some examples of the method, apparatuses, and non-transitory computer-readable medium described herein, determining statistical information further may include operations, features, means, or instructions for determining a standard deviation of the set of measured values over the period of time, and determining a set of demarcation points based on a function of the standard deviation, where the set of adjusted values may be based on the set of demarcation points.

In some examples of the method, apparatuses, and non-transitory computer-readable medium described herein, adjusting the set of measured values to the set of adjusted values further may include operations, features, means, or instructions for rounding each value of the set of measured values to a nearest value within the set of demarcation points.

In sonic examples of the method, apparatuses, and non-transitory computer-readable medium described herein, the set of display values includes a temporally first value from the set of adjusted values, a temporally middle value from the set of adjusted values, and a temporally last value from the set of adjusted values.

In some examples of the method, apparatuses, and non-transitory computer-readable medium described herein, the set of display values includes one or more extrema from the set of adjusted values.

In some examples of the method, apparatuses, and non-transitory computer-readable medium described herein, displaying the graphical representation of the set of display values further may include operations, features, means, or instructions for displaying each display value of the set of display values according to a temporal order of the corresponding measured values.

Some examples of the method, apparatuses, and non-transitory computer-readable medium described herein may further include operations, features, means, or instructions for determining a median value of the set of adjusted values, where the set of display values may be the median value, determining a first difference between the median value and a maximum value of the set of adjusted values, and determining a second difference between the median value and a minimum value of the set of adjusted values, where displaying the graphical representation of the set of display values includes displaying the median value with a first error bar corresponding to the first difference and second error bar corresponding to the second difference.

Some examples of the method, apparatuses, and non-transitory computer-readable medium described herein may further include operations, features, means, or instructions for calculating a predicted future value for the physiological parameter by inputting the set of measured values into an early warning function, and generating a warning indicating a potential health threat based on the predicted future value.

DETAILED DESCRIPTION

Figure 1:
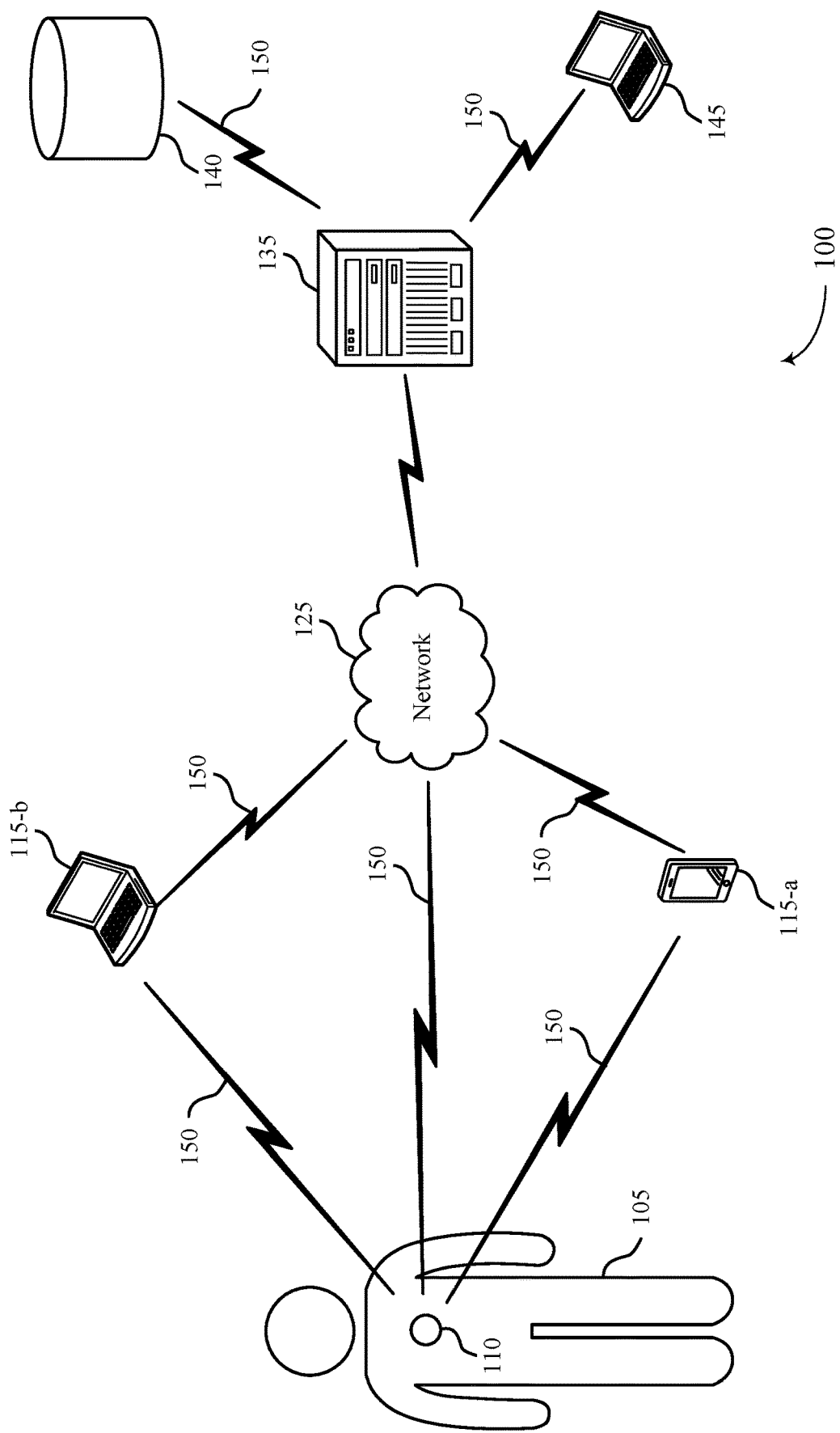
FIG. 1 illustrates an example of a system for patient monitoring that supports contextual patient data representation and display in accordance with aspects of the present disclosure.

In a healthcare facility, data related to a patient may be displayed at a computing device (such as a bedside monitor, a central nurse station). A user (e.g., a doctor, nurse, or other healthcare provider) may review the display of the computing device in order to determine a health status of the patient. The health status may indicate how the patient is trending (e.g., the health of the patient over time). In some cases, the data displayed at the computing device may not provide the data required (or present the data in such a way) for the user to determine the health status accurately and/or efficiently. For example, the data displayed at the computing device may be data based on a monitored physiological parameter. The data may include noise that prevents the user from objectively analyzing the data. In some other examples, the data may be overly simplified. That is, the simplification may remove important context. For example, simplified data including a single directional arrow (e.g., corresponding to the trend of the data from a previously-measured value) may not distinguish between a steady decline over 4 hours or a significant decline 3.9 hours ago followed by stability. Further, the data displayed at the computing device may not include relevant information as it relates to a patient health record. Instead the patient health record may be included in an electronic medical record (EMR) or a paper file associated with the patient, but not easily accessible by a user at the computing device. The user may have to sort through multiple sources (e.g., the EMR, the paper file) in order to see data associated with the patient's health record. In some cases, this may prevent the user from accurately or efficiently determining a health status of a patient.

The computing device may display simplified data that provides relevant context on a computing device. The data, which may be based on a monitored physiological parameter, may be simplified by filtering and/or adjusting the measured physiological data. The data may be filtered by a low-pass filter e.g., to decrease noise). For example, the data may be processed by an averaging window (e.g., a 1 minute averaging window applied to data taken every 5 seconds). The data may further be processed according to some demarcation points. That is, the data may be rounded to a nearest demarcation point in order to further eliminate noise. In some cases, the demarcation points may correspond to known standard deviations for the physiological data (e.g., according to the demographic information of the patient). For example, if a standard deviation of oxygen saturation (e.g., as measured by a pulse oximeter) is 3% and an average value of oxygen saturation for a person with similar demographic information to the patient is 95%, the demarcation points may include 92%, 95%, and 98%. In sonic other examples, the demarcation points may correspond to a function of the known standard deviations (e.g., half of a standard deviation). The computing device may display a subset of the simplified data. For example, if the simplified data includes data taken every 5 seconds over an 8 hour period, the computing device may display only a portion of those data points. The displayed data may include data from throughout the 8 hour period (e.g., at hour 1, hour 4, and hour 8) as well as local extrema within the 8 hour period (e.g., a relative maximum value, a relative minimum value). The data may be displayed as a line graph, where each data point is organized temporally and connected to the neighboring data points via a line.

The computing device may display one or more icons at the computing device in order to provide data at the computing device related to the health record of the patient. The icons may provide a visual indicator of certain data related to the patient's health record. For example, an icon may indicate known patient conditions (e.g., the patient has chronic obstructive pulmonary disease (COPD)), computed risk factors (e.g., risk of mortality, risk of sepsis), allergies (e.g., allergies to medications), prior medications (e.g., blood thinners), active medications (e.g., opioids), prior surgeries (e.g., open heart surgery), or organ conditions (e.g., having donated, having received). The set of icons displayed at the computing device may be configured based on the user (e.g., a doctor vs. a nurse) or a category of the icon (e.g., cardiac, respiratory, pre-existing conditions, allergies). In some cases, the icon may indicate additional patient-specific information. For example, the icon may indicate a type of allergic reaction specific to the patient, a dosage for a medication, etc. In some other cases, the icon may further indicate suggested care. For example, the icon may indicate that the patient has COPD and the suggested care includes supplemental oxygen.

Displaying the simplified data along with a visual representation of some health record data may allow a user to more accurately and efficiently determine the health status of a patient.

Aspects of the disclosure are initially described in the context of a wireless patient monitoring system. Aspects of the disclosure are further illustrated by and described with reference to apparatus diagrams, system diagrams, and flowcharts that relate to patient specific alarm thresholds.

FIG. 1 illustrates an example of a wireless patient monitoring system 100 in accordance with various embodiments of the present disclosure. The wireless patient monitoring system 100 may include a patient 105 wearing, carrying, or otherwise coupled with a medical device 110. Although a single medical device 110 is shown, multiple medical devices 110 may be coupled to the patient 105. The patient 105 may be a patient in a hospital, nursing home, home care, a medical facility, or another care facility. The medical device 110 may transmit signals via wireless communications links 150 to computing devices 115 or to a network 125.

The medical device 110 may include one or more sensors configured to collect a variety of physiological parameters as well as information related to the location and movement of the patient 105. For example, the medical device 110 may include a pulse oximetry (SpO2) sensor, a capnography sensor, a heart rate sensor, a blood pressure sensor, an electrocardiogram (ECG) sensor, a respiratory rate sensor, a glucose level sensor, a depth of consciousness sensor, a body temperature sensor, an accelerometer, a global positioning sensor, a sensor which triangulates position from multiple local computing devices 115, or any other sensor configured to collect physiological, location, or motion data associated with the patient 105.

The medical device 110 may be coupled with the patient 105 in a variety of ways depending on the data being collected. For example, the medical device 110 may be directly coupled with the patient 105 (e.g., physically connected to the patient's chest, worn around the patient's wrist, attached to the patient's finger, or positioned over the patients nose or mouth). The data collected by the medical device 110 may be wirelessly transmitted to either the computing devices 115 or to the remote computing device 145 (via the network 125 and central station 135). Data transmission may occur via, for example, frequencies appropriate for a personal area network (such as Bluetooth, Bluetooth Low Energy (BLE), or IR communications) or local (e.g., wireless local area network (WLAN) or wide area network (WAN) frequencies such as radio frequencies specified by IEEE standards (e.g., IEEE 802.15.4 standard, IEEE 802.11 standard (Wi-Fi), IEEE 802.16 standard (WiMAX), etc.).

Computing device 115-a may be a wireless device such as a tablet, cellular phone, personal digital assistant (PDA), a dedicated receiver, or other similar device or a spatially distributed network of devices configured to receive signals from the medical device 110. Computing device 115-b may be a wireless laptop computer, a clinician Workstation on Wheels, or a smart hospital bed configured to receive signals from the medical device 110. The computing devices 115 may be in communication with a central station 135 via network 125.

The medical device 110 may also communicate directly with the central station 135 via the network 125. The central station 135 may be a server or a central nurse station located within the hospital or in a remote location. The central station 135 may be in further communication with one or more remote computing devices 145, thereby allowing a clinician to remotely monitor the patient 105. The central station 135 may also be in communication with various remote databases 140 where the collected patient data may be stored. In sonic cases, the remote databases 140 include electronic medical records (EMR) applications for storing and sharing patient data.

In accordance with various embodiments, methods and apparatuses are described for contextual patient data representation and display. For example, a user (e.g., a doctor, nurse, or other healthcare provider) may review the display of the computing device 115-b in order to determine a health status of the patient 105. The computing device 115-b may display data that provides relevant context. The data, which may be based on a monitored physiological parameter measured by medical device 110, may be simplified by filtering and/or adjusting the measured physiological data. The data may be filtered by a low-pass filter (e.g., to decrease noise). For example, the data may be processed by an averaging window (e.g., a 1 minute averaging window applied to data taken every 5 seconds). The data may further be processed according to some demarcation points. That is, the data may be rounded to a nearest demarcation point in order to further eliminate noise. In some cases, the demarcation points may correspond to known standard deviations for the physiological data (e.g., according to the demographic information of the patient 105). For example, if a standard deviation of oxygen saturation (e.g., as measured by a pulse oximeter) is 3% and an average value of oxygen saturation for a person with similar demographic information to the patient is 95%, the demarcation points may include 92%, 95%, and 98%. In some other examples, the demarcation points may correspond to a function of the known standard deviations (e.g., half of a standard deviation). The computing device 115-b may display a subset of the simplified data. For example, if the simplified data includes data taken every 5 seconds over an 8 hour period, the computing device may display only a portion of those data points. The displayed data may include data from throughout the 8 hour period (e.g., at hour 1, hour 4, and hour 8) as well as local extrema within the 8 hour period (e.g., a relative maximum value, a relative minimum value). The data may be displayed as a line graph, where each data point is organized temporally and connected to the neighboring data points via a line.

The computing device 115-b may display one or more icons in order to provide context related to the health record of the patient 105. The icons may provide a visual indicator of certain data related to the patient's health record. For example, an icon may indicate known patient conditions (e.g., the patient 105 has chronic obstructive pulmonary disease (COPD)), computed risk factors e.g., risk of mortality, risk of sepsis), allergies (e.g., allergies to medications), prior medications (e.g., blood thinners), active medications (e.g., opioids), prior surgeries (e.g., open heart surgery), or organ conditions (e.g., having donated, having received). The set of icons displayed at the computing device 115-b may be configured based on the user (e.g., a doctor vs. a nurse) or a category of the icon (e.g., cardiac, respiratory, pre-existing conditions, allergies). In some cases, the icon may indicate additional patient-specific information. For example, the icon may indicate a type of allergic reaction specific to the patient 105, a dosage for a medication, etc. In some other cases, the icon may further indicate suggested care. For example, the icon may indicate that the patient 105 has COPD and the suggested care includes supplemental oxygen.

Figure 2:
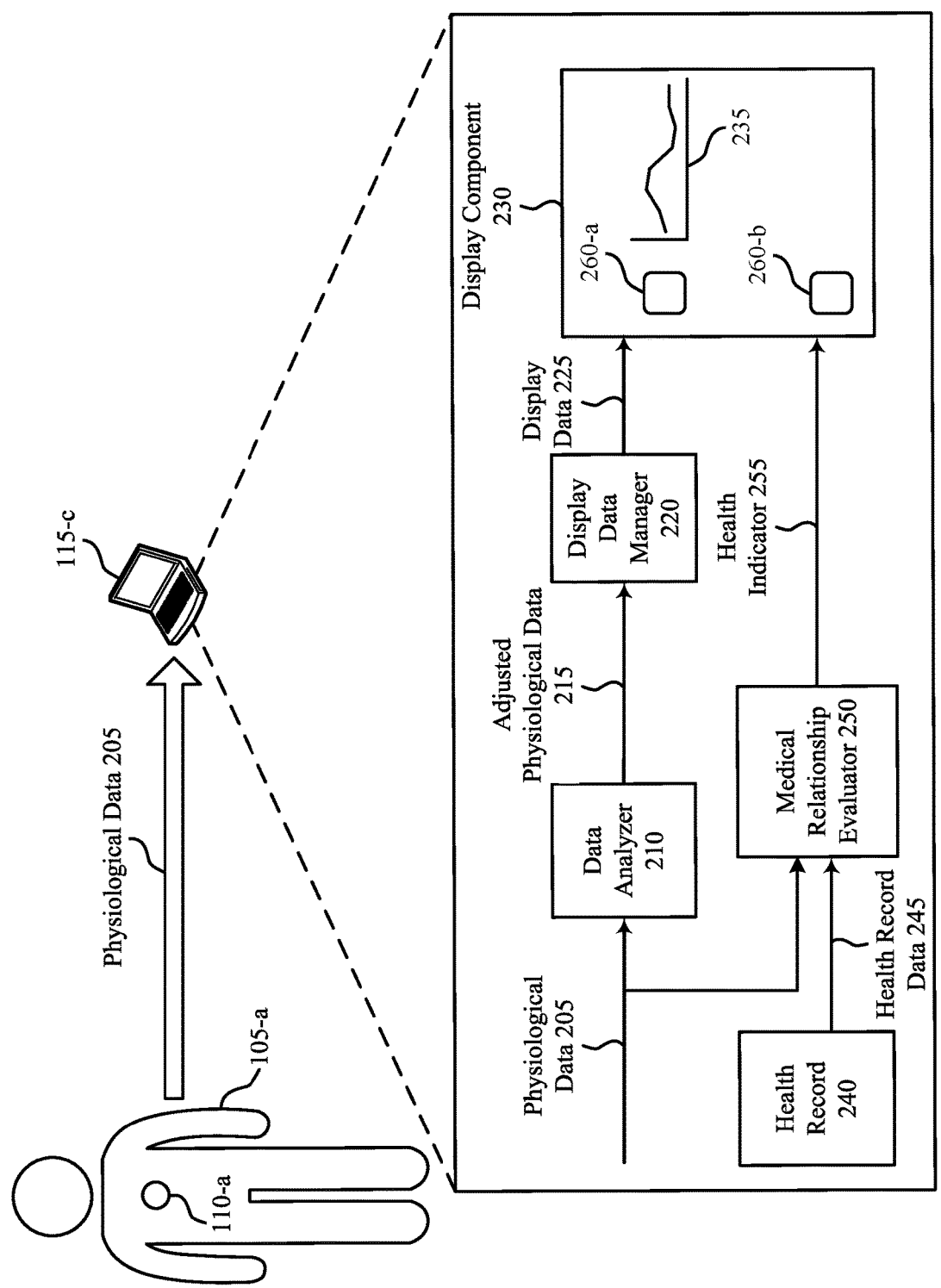
FIG. 2 illustrates an example of a system that supports contextual patient data representation and display in accordance with aspects of the present disclosure.

FIG. 2 illustrates an example of a system 200 that supports contextual patient data representation and display in accordance with aspects of the present disclosure. In some examples, system 200 may implement aspects of wireless patient monitoring system 100 and may include a patient 105-*a* wearing, carrying, or otherwise coupled with a medical device 110-*a*. System 200 may be in communication with computing device 115-*c*, which may be a patient bedside monitor. Computing device 115-*c* may include a data analyzer 210, a display data manager 220, a health record 240, a medical relationship evaluator 250, and a display component 230.

The computing device 115-*c* may receive physiological data 205 from the patient 105-*a*. In some cases, the physiological data 205 may he data collected by a medical device 110-*a* measuring a corresponding physiological parameter. For example, the physiological data 205 may correspond to a physiological parameter such as heart rate and the medical device 110-*a* may be an electrocardiogram. In another example, the physiological data 205 may corresponding to a physiological parameter such as oxygen saturation levels (e.g., pulse oximetry) and the medical device 110-*a* may be a pulse oximeter. The physiological data 205 may be a stream of raw data (corresponding to a measured value of the physiological parameter), sent periodically over time. For example, the physiological data 205 may be sent to the computing device 115-*c* every 10 seconds with an updated measured value. In some cases, the patient 105-*a* may be coupled with more than one medical device 110-*a* (e.g., measuring more than one physiological parameter). That is, the physiological data 205 may contain more than one type of physiological data (e.g., heart rate data and oxygen saturation levels).

The data analyzer 210 may receive the physiological data 205. In some cases, the data analyzer 210 may analyze and process the physiological data 205 in order to more effectively communicate the health of the patient to a user (e.g., a healthcare provider). The data analyzer 210 may categorize the physiological data 205. For example, the data analyzer 210 may classify physiological data 205 measuring heart rate as belonging to a cardiac category. Alternatively, the data analyzer 210 may classify physiological data 205 measuring respiratory rate as belonging to a ventilation category. In some cases, each category may correspond to a different display color for representation at the display component 230. For example, a representation of physiological data 205 belonging to a cardiac category may be red while a representation of physiological data 205 belonging to a ventilation category may be blue.

The data analyzer 210 may analyze the physiological data 205 to detect events that may be dangerous to the patient. For example, there may be a behavior of the physiological data 205 that indicates a dangerous event for the patient (e.g., a heart rate above a certain threshold, a change in oxygen saturation level within a certain time). The data analyzer 210 may utilize a configurable function to detect potentially dangerous events indicated by the physiological data 205. In some cases, the function may include a summation or a probability combination of the physiological data 205. A potentially dangerous event may be detected based on a threshold or alarming target, which may be based on an output of the function. In the event that the data analyzer 210 detects a potentially dangerous event, the data analyzer 210 may indicate the event to an early warning system, which may in turn indicate the potentially dangerous event to a user (e.g., a healthcare provider).

The data analyzer 210 may work in conjunction with the display data manager 220 and the display component 230 in order to display a representation of the physiological data 205 (e.g., graph 235) that may he efficiently and accurately analyzed by a health care provider. The data analyzer 210 may process the physiological data 205 to produce adjusted physiological data 215 (e.g., in order to more effectively communicate the data to the user). In some cases, the adjusted physiological data 215 may be a filtered version of the physiological data 205. For example, the data analyzer 210 may include a low pass filter such as an averaging window. That is, if the physiological data 205 includes data values taken every 5 seconds, the data analyzer 210 may use a 1-minute averaging window, to condense 11 data values (e.g., taken over the course of a minute) into a single data point determined based on the average of each of the 11 data values. In some cases, the data analyzer 210 may recalculate an average over the averaging window at a configured recalculation frequency. For example, if the configured recalculation frequency is 15 seconds, the data analyzer 210 may recalculate an average value over the configured averaging window every 15 seconds. The configured recalculation frequency and the length of the averaging window may be configurable. That is, a user (e.g., a doctor, a nurse) may adjust these values.

The data analyzer 210 may further process the physiological data 205 according to some demarcation points. That is, the data analyzer 210 may include a discreet set of demarcation points determined based on the type of physiologic data being measured. In some cases, the demarcation points may further depend on the demographics of the patient (e.g., the age, weight, gender of the patient). The data analyzer 210 may sort each of the types of physiological data 205 according to the demarcation points. That is, the data analyzer 210 may round each of the physiological data values to a nearest demarcation point. This may further eliminate noise while still conveying essential information to a healthcare provider (e.g., a doctor, a nurse). In some instances, the data analyzer 210 may sort previously-filtered physiological data 205 (e.g., data that has been filtered according to an averaging window as discussed herein).

The demarcation points may correspond to known standard deviations for the physiological data (e.g., for the patient 105-*a*). For example, if a standard deviation of oxygen saturation (e.g., as measured by a pulse oximeter) is 3% and an average value of oxygen saturation for the patient is 95%, the demarcation points may include 92%, 95%, and 98%. In some other examples, the demarcation points may correspond to a function of the known standard deviations (e.g., half of a standard deviation). The demarcation points used for the physiological data 205 may be configurable by a user.

The data analyzer 210 may output the adjusted physiological data 215. The adjusted physiological data 215 may be sorted (e.g., according to configured demarcation points) and/or filtered (e.g., using a low-pass filter such as an averaging window). The adjusted physiological data 215 may be output to a display data manager 220. The display data manager 220 may determine a method for displaying information contained within the physiological data 205. In some cases, oversimplifying the physiological data 205 for displaying may prevent a health care provider from accurately determining a health status for the patient. Alternatively, too much data (e.g., not simplified enough) may require a health care provider to interpret the data, which may increase subjectivity in analyzing a patient's health condition.

The display data manager 220 may determine some display data 225 based on the adjusted physiological data 215 for displaying at the display component 230 in graph 235, for example. The graph 235 may show the display data 225 across a configurable time window (e.g., 3 hours). In some cases, the display data 225 may include a subset of the adjusted physiological data 215. The subset may include values from the adjusted physiological data 215 taken at times throughout the configurable time window (e.g., at the beginning, at the middle, at the end). The subset may further include extreme values occurring during the configurable window (e.g., a maximum value, a minimum value). In some other cases, the subset may include a single value (e.g., corresponding to an average value, a median value). In the case of the subset including a single value, the display data 225 may include error bars showing the extremes during the configurable time window (e.g., the maximum and minimum values of the adjusted physiological data 215 during the configurable time window). The display data 225 may further include a baseline indicating an expected value for the physiological parameter being measured by the medical device 110-a. In some cases, the expected value may be tailored to the patient 105-a (e.g., based on patient demographics as indicated by the health record 240). For example, if the physiological parameter being measured is heart rate, the expected value for the heart rate may be 90 bpm for a 40-year-old male patient, but 75 bpm for a 75-year-old male patient.

The graph 235 may be color coded according to the category of the physiological data 205 being represented by the graph 235 (e.g., as determined by the data analyzer 210). For example, if the graph 235 represents blood pressure data, the data may be represented in a red color according to a cardiac category. In another example, if the graph 235 represents glucose levels, the graph 235 may be a green color according to a blood test category.

The health record 240 may include data related to the patient 105-a. In some cases, the health record 240 may include demographics data for the patient 105-a. For example, the health record 240 may include data such as the age, gender, and/or weight of the patient 105-a. In some other cases, the health record 240 may include data collected by a health care provider prior to a collection of physiological data 205. Additionally or alternatively, the health record 240 may include data within an electronic medical record (EMR) of the patient 105-a. For example, the health record 240 may include information related to known patient conditions (e.g., the patient has chronic obstructive pulmonary disease (COPD), asthma), computed risk factors (e.g., risk of mortality, risk of sepsis), allergies (e.g., allergies to medications), prior medications e.g., blood thinners), active medications (e.g., opioids), prior surgeries (e.g., open heart surgery), or organ conditions (e.g., having donated, having received). The health record 240 may categorize the data. For example, a previous heart surgery may be associated with a cardiac category, while COPD information may be associated with a ventilation category. In some cases, each category may correspond to a different display color for representation at the display component 230. For example, a representation of health record 240 data belonging to a cardiac category may be red while a representation of health record 240 data belonging to a ventilation category may be blue.

The medical relationship evaluator 250 may receive health record data 245 from the health record 240. The medical relationship evaluator 250 may determine a set of data from the health record 240 to display at the display component 230. In some cases, the set of data to be displayed at the display component 230 may be a default set (e.g., any allergies to medications, any known patient conditions). In some other cases, the set of data to be displayed at the display component 230 may be based on received configurations (e.g., as received from a healthcare provider such as a nurse or a doctor). The medical relationship evaluator 250 may output a health indicator 255 corresponding to each piece of data from the health record 240 (e.g., within the set of data). The health indicator 255 may correspond to an icon 260 (e.g., a badge), where the icon 260 is a visual representation of the piece of data form the health record 240.

The medical relationship evaluator 250 may determine a position for each icon 260 on the display component 230. In some cases, there may be a separate display screen (e.g., within the display component 230) for the icons 260. That is, other data displayed at the display component 230 (e.g., display data 225) may be displayed on a first screen while the icons 260 may be displayed on a second screen. The separate display screen may decrease an amount of information on each screen. The decreased amount of data on each screen may allow a health care provider to process the information displayed on each screen more efficiently (e.g., due to less perceived clutter). In some other cases, the position for each icon 260 may be based on an unused portion of the display component 230. An unused portion of the display component 230 may be a portion of the display component 230 that is not used to display a representation of physiological data 205. For example, the border of the display component 230 may be unused. Here, the icons 260 may be positioned along the border.

In some other cases, the position for each icon 260 may he based on a relationship between the physiological data 205 and the health record data 245 indicated by the icon 260. The medical relationship evaluator 250 may determine the medical relationship between each icon 260 and the physiological data 205. In the event that health record 245 data indicated by the icon 260 has a medical relationship with the physiological data 205, the icon 260 may be positioned within a threshold distance of the graph 235 displaying information related to the physiological data 205. For example, if an icon 260-a indicates that patient 105-a has COPD, the medical relationship evaluator 250 may determine a medical relationship with physiological data 205 that relates to oxygen saturation levels. Therefore, the medical relationship evaluator 250 may determine to position the icon 260-a within a threshold distance of the graph 235 (which displays information related to the oxygen saturation levels.

In the event that the health record data indicated by the icon 260 does not have a medical relationship with the physiological data 205, the icon 260 may be positioned outside of a threshold distance of the graph 235 displaying information related to the physiological data 205. For example, if an icon 260-b indicates that the patient 105-b is allergic to penicillin, the medical relationship evaluator 250 may determine there is no medical relationship with physiological data 205 that relates to oxygen saturation levels. Therefore, the medical relationship evaluator 250 may determine to position the icon 260-b outside of a threshold distance from the graph 235. In some cases, icons 260 that do not have a medical relationship with other displayed data may be displayed on a separate page.

Figure 3A:
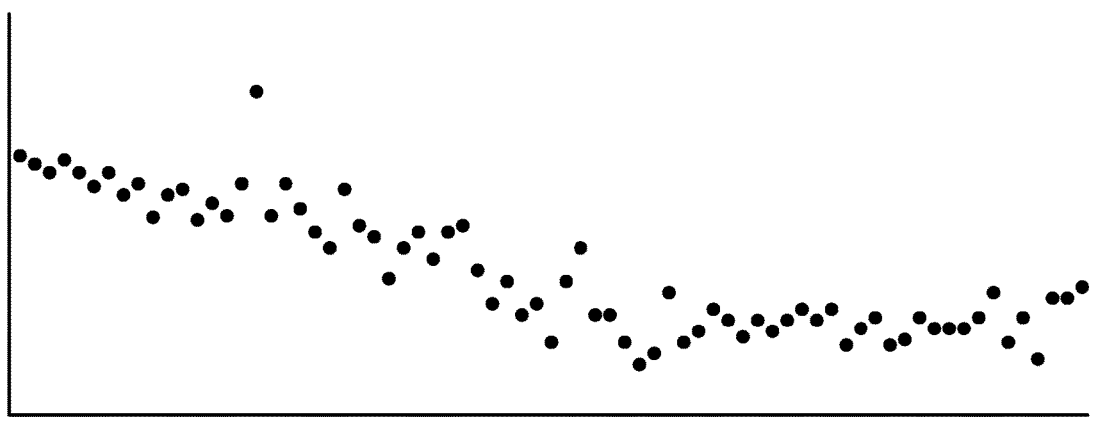
FIGS. 3A-3C illustrate examples of data analysis configurations that supports contextual patient data representation and display in accordance with aspects of the present disclosure.
Figure 3B:
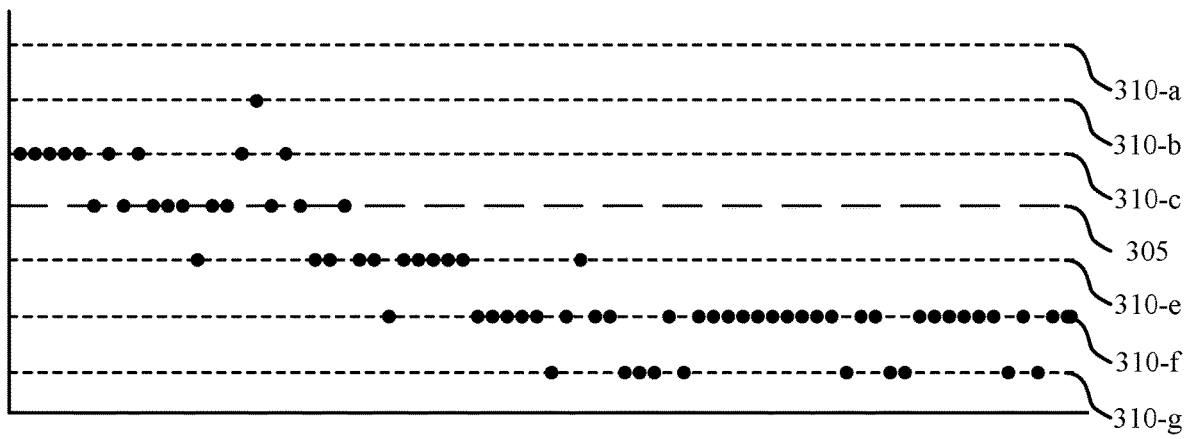
Figure 3C:
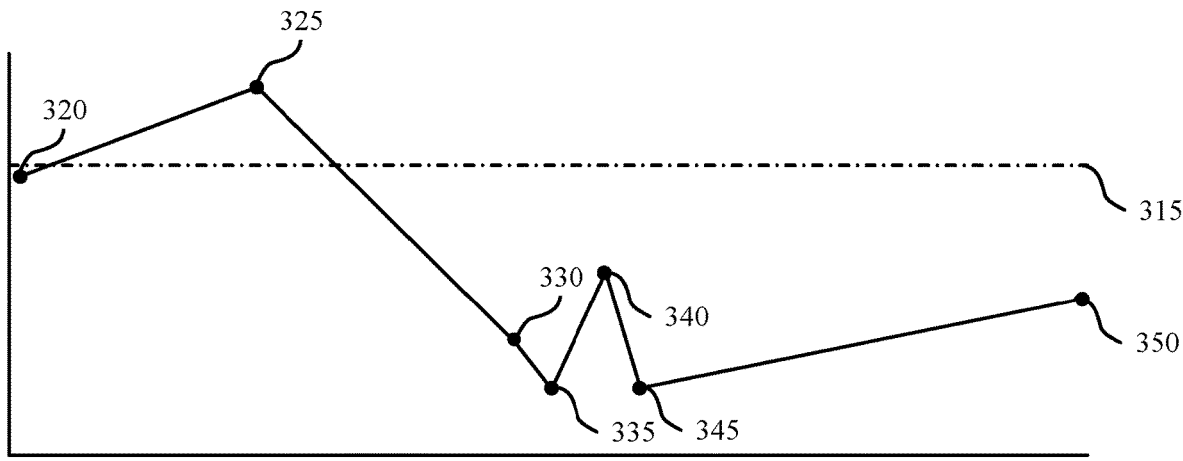

FIGS. 3A, 3B, and 3C illustrate examples of data analysis configurations 300-a, 300-b, and 300-c that support contextual patient data representation and display in accordance with aspects of the present disclosure. In some examples, data analysis configurations 300-a, 300-b, and 300-c may implement aspects of wireless patient monitoring system 100. Data analysis configurations 300-a, 300-b, and 300-c may include aspects of system 200. For example, the data analyzer 210 at the computing device 115-c may use one or more of the data analysis configurations 300-a, 300-b, and/or 300-c on physiological data 205.

The data analysis configurations 300-a, 300-b, and 300-c may include an x-axis that represents time. The data analysis configurations 300 may show data within a time window. For example, the data analysis configurations 300 may show data within an 8 hour time window. In some cases, the time window may be configurable (e.g., by a healthcare provider). The y-axis may represent a value corresponding to physiological data (e.g., such as physiological data 205 as discussed with reference to FIG. 2). In some cases, the computing device 115-c may receive more than one set of physiological data (e.g., corresponding to more than one physiological parameter). Here, the computing device (such as computing device 115-c) may use one or more of the data analysis configurations 300-a, 300-b, and/or 300-c on each of the sets of physiological data separately.

Data analysis configuration 300-a may show data corresponding to a measured or filtered value of a physiological parameter (e.g., physiological data 205, adjusted physiological data 215). In some cases, the data may correspond to the measured value of a physiological parameter. In some other cases, the data may correspond to the filtered values of the physiological parameter (e.g., data that has been filtered according to an averaging window as discussed with reference to FIG. 2). The data analysis configurations 300 may demonstrate a method for processing received physiological data and displaying a graphical representation of the physiological data that may be efficiently and accurately reviewed by a health care provider. For example, the data analysis configuration 300-c may be an example data analysis configuration 300 that provides context regarding a trend of the physiological data over time while minimizing an amount of noise.

Data analysis configuration 300-b may show an adjusted version of the data displayed within data analysis configuration 300-a. For example, the data displayed within data analysis configuration 300-a may be adjusted based on one or more demarcation points 310. The demarcation points 310 may be configurable or may be preconfigured at the computing device. In some cases, the configured or preconfigured values of the demarcation points 310 may correspond to a known standard deviation of the physiological data. For example, there may be a standard deviation known (e.g., based on previous data from other patients) for the physiological parameter of patients within the same demographics as the patient (e.g., patient 105-a). Here, data analysis configuration 300-b may include a value 305-a that corresponds to a median value of the physiological data (e.g., physiological data 205). In some other cases, value 305-a may correspond to an average value of the physiological data, an average value of the data displayed at data analysis configuration 300-a, or a known average or median value of the physiological data (e.g., as indicated based on data for other patients with similar demographics). Demarcation points 310-e and 310-c may correspond to values that are one standard deviation away from the value 305-a. Demarcation points 310-b and 310-f may correspond to values two standard deviations away from the value 305-a. Demarcation points 310-a and 310-g may correspond to values three standard deviations away from the value 305-a. In some cases, the demarcation points 310 may be functions of the expected standard deviation (e.g., ½ of the standard deviation, ¼ of the standard deviation).

The data displayed within data analysis configuration 300-a may be rounded to a nearest demarcation point 310 in the data analysis configuration 300-b. That is, the range of measured or averaged values displayed at data analysis configuration 300-a may be rounded to a discreet number of demarcation points. This may further eliminate noise while still conveying essential information to a healthcare provider (e.g., a doctor, a nurse).

The data analysis configuration 300-c may show data corresponding to display data (e.g., display data 225 as discussed with reference to FIG. 2). The display data may include a subset of the data at data analysis configuration 300-b. In some cases, the subset of data may be derived by breaking the time window into one or more time segments. A time segment may be a fraction of the total time window represented by the data analysis configuration 300-c. That is, a time segment may be one half of the total time window, one third of the total time window, or the entirety of the total time window. The subset may include a set of data points from each time segment. For example, the subset may include initial and final values of each time segment as well as local extrema within each time segment. Here, subset of data breaks the window into two time segments, although in other cases, the subset of data may be broken into a single time segment or more than two time segments. The display data includes a starting point 320 (e.g., corresponding to the temporally first value of data analysis configuration 300-h, a middle point 335 (e.g., corresponding to the temporally middle value of data analysis configuration 300-b), and an end point 350 (e.g., corresponding to the temporally last value of data analysis configuration 300-b). The display data further includes a maximum and minimum value within each time segment of the time window. For example, point 325 may correspond to the maximum value within the first segment of the time window while point 330 corresponds to the minimum value within the first segment of the time window. Further, point 340 may correspond to the maximum value within the second segment of the time window while point 345 corresponds to the minimum value within the second segment of the time window. The data analysis configuration 300-c may include a line 315 corresponding to an expected value of the physiological data (e.g., a baseline value indicating a "normal" value for the physiological parameter). The expected value may be based on the demographics for the patient.

Figure 4:
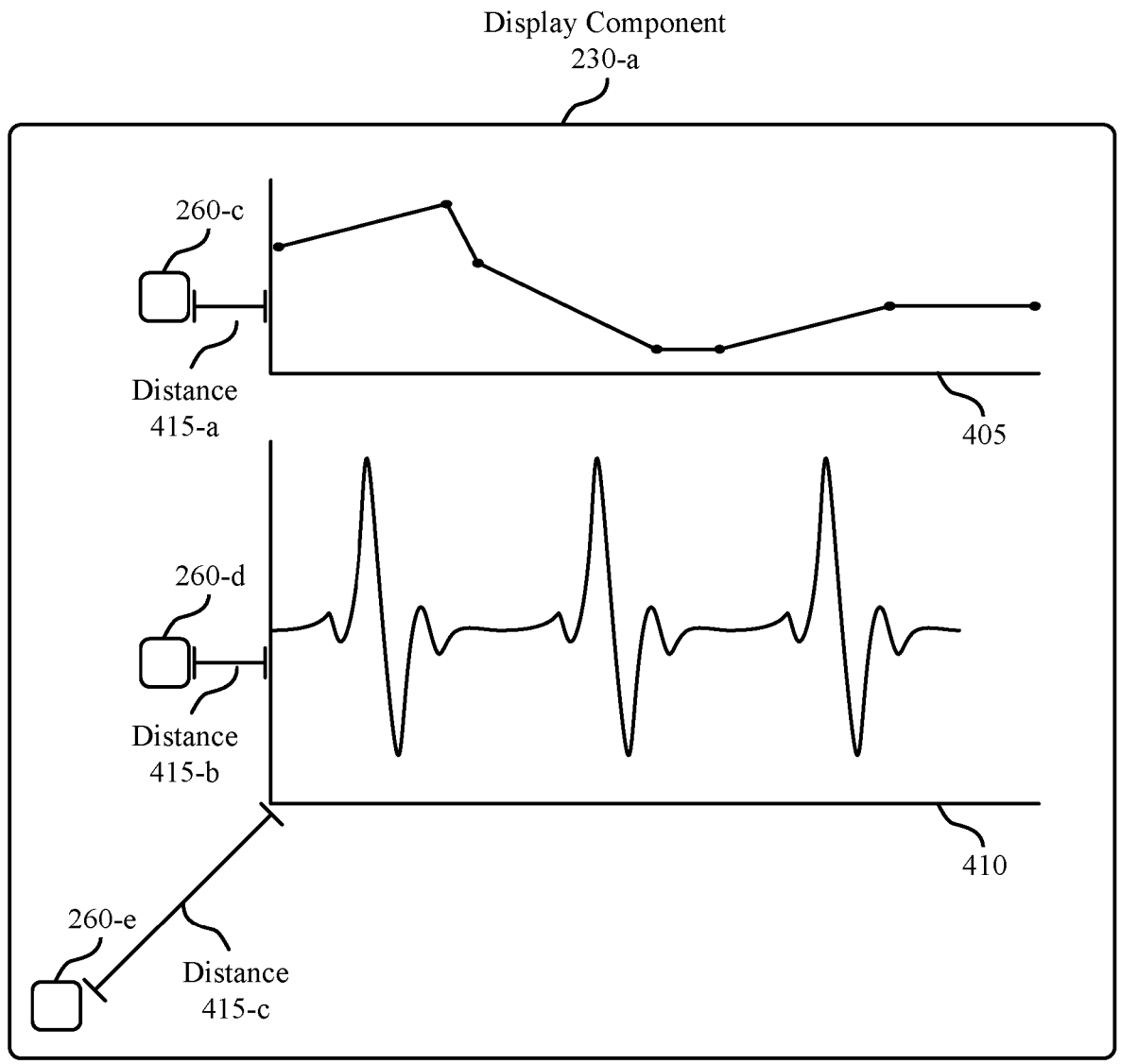
FIG. 4 illustrates an example of a system that supports contextual patient data representation and display in accordance with aspects of the present disclosure.

FIG. 4 illustrates an example of system 400 that supports contextual patient data representation and display in accordance with aspects of the present disclosure. In some examples, system 400 may implement aspects of wireless patient monitoring system 100, system 200, and data analysis configurations 300. For example, the display component 230-a may be an example of display component 230 as discussed with reference to FIG. 2. In some other examples, graph 405 may implement one or more data analysis configurations 300 as discussed with reference to FIG. 3.

The display component 230-a may include graphs 405 and 410. Graphs 405 and 410 may each represent physiological data (e.g., physiological data 205) acquired by measuring a physiological parameter of a patient. The icons 260 may represent a health indicator corresponding to some data related to a health record of the patient. In some cases, an icon 260 may be generic. For example, the icon 260 may indicate a pre-existing condition for the patient (e.g., the patient has COPD). In another example, the icon 260 may indicate allergies (e.g., the patient is allergic to latex). In some other cases, the icon 260 may be patient-specific. For example, the icon 260 may indicate that the patient has COPD with a lung capacity of 3 liters. In another example, the icon 260 may indicate that the patient is allergic to latex with a reaction including hives. In some other cases, the icon 260 may by advisory (e.g., including a suggested care step). For example, the icon 260 may indicate that the patient has COPD with suggested care including supplemental oxygen. In some cases, the icon 260 may interactively provide a user (e.g., a healthcare provider) with additional information. For example, a user may hover or click on the icon 260 (e.g., using a mouse, using a touch screen) to determine additional information about the health record data indicated by the icon 260.

The icons 260 may be positioned based on a medical relationship (e.g., as determined by a medical relationship evaluator as discussed with reference to FIG. 2) between each icon and other physiological data displayed by display component 230. Here, icons 260-*c* and 260-*d* may be positioned distances 415-*a* and 415-*b* away from graphs 405 and 410 respectively. The distances 415-*a* and 415-*b* may be within a threshold distance. Placing icons 260 within a threshold distance of displayed physiological data (e.g., graphs 405, 410) may indicate a medical relationship between the icons 260 and the displayed physiological data. For example, icon 260-*c* may indicate that a patient has COPD, while graph 405 may display a patient's oxygen saturation levels (which may be impacted by COPD). In another example, icon 260-*d* may indicate that a patient had heart surgery, while graph 410 displays a heart rhythm (which may be impacted by the heart surgery). However, the icon 260-*e* may be placed at a distance 415-*c* from graph 410. If distance 415-*c* exceeds the threshold distance, this may indicate that the data indicated by the icon 260-*e* does not affect the physiological data displayed by graph 410. For example, icon 260-*e* may indicate that a patient is allergic to penicillin. However, the medical relationship evaluator may determine that the allergy does not affect the patient's heart rhythm and as such, may display the icon 260-*e* at a distance 415-*c* (which may be outside of the threshold distance) away from the graph 410.

The icons 260 displayed at the display component 230-*a* may be configurable. For example, a healthcare provider may determine a subset of icons to view when evaluating a patient. In some cases, the subset of icons 260 displayed at the display component 230-*a* may be based on the type of health care provider evaluating the patient. For example, the set of icons 260 displayed when a nurse is evaluating the patient may be different than the set of icons 260 displayed when a doctor is evaluating the patient. In other cases, the set of icons may be based on a selected viewing category (e.g., a healthcare provider may select a category of icons to view). For example, the categories may include filtering icons 260 based on demographic information, respiratory information, cardiac information, etc. Additionally or alternatively, a user may enable or disable the display of icons 260.

Figure 5:
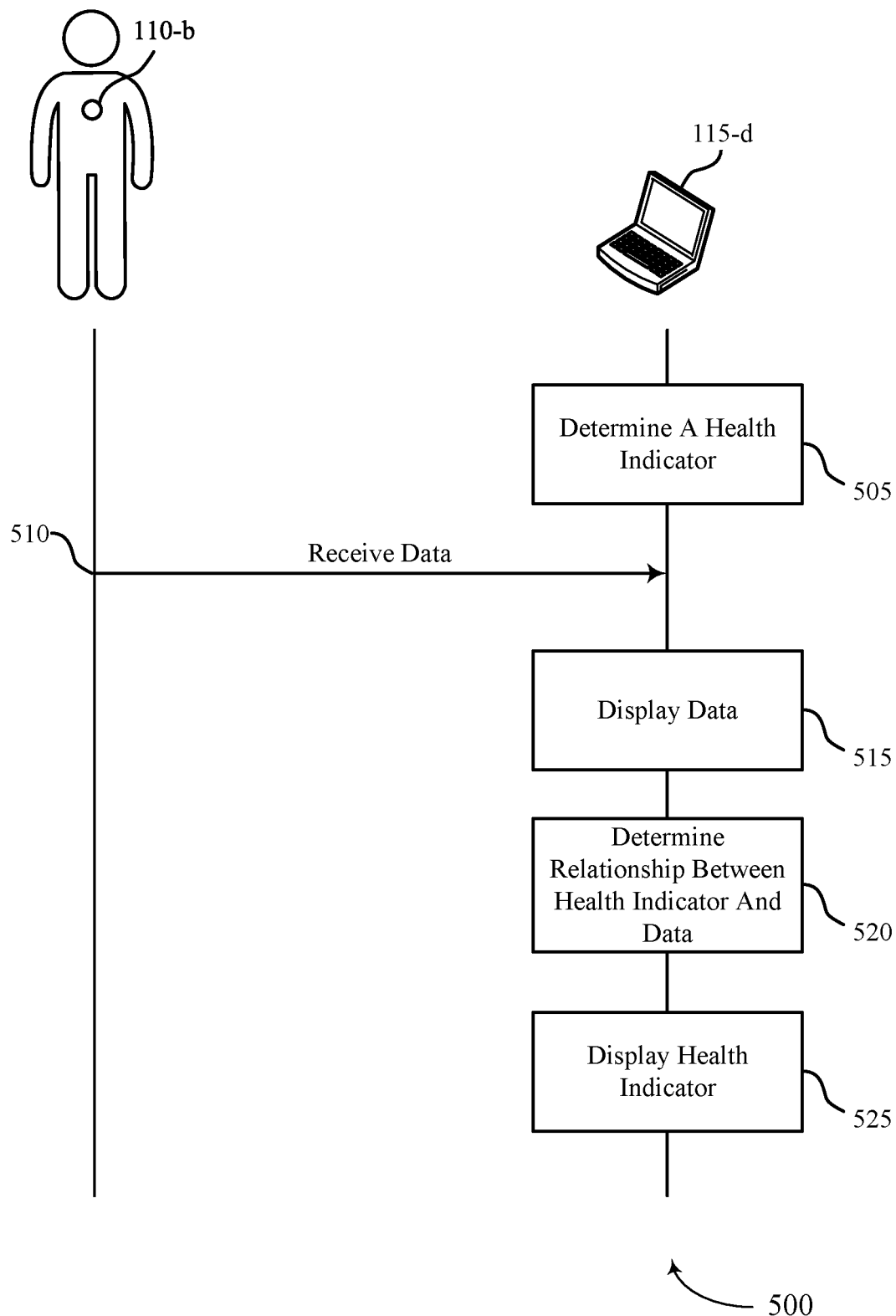
FIGS. 5 and 6 illustrate examples of process flows that supports contextual patient data representation and display in accordance with aspects of the present disclosure.

FIG. 5 illustrates an example of a process flow 500 that supports contextual patient data representation and display in accordance with aspects of the present disclosure. Process flow 500 may include computing device 115-*d* and medical device 110-*b*, which may be respective examples of computing device 115 and medical device 110 as described with reference to FIGS. 1-2. The computing device 115-*d* may be an example of a central station or a monitor as described herein. Alternative examples of the following may be implemented, where some steps are performed in a different order or not at all. Some steps may additionally include features not mentioned above.

At block 505, the computing device 115-*d* may determine a health indicator for visually representing data related to a health record of the patient. In some examples, the data represented by the health indicator corresponds to a patient condition, a risk factor for the patient, a current medication of the patient, or a combination thereof. In some cases, the health indicator comprises an icon indicating the data related to the health record of the patient and a suggested health action based on the data related to the health record.

At block 510, the computing device 115-*d* may receive, from the medical device 110-*b*, current data corresponding to a monitored physiological parameter. The current data may be received after the computing device 115-*d* determined the health indicator.

At block 515, the computing device 115-*d* may display, at a first location on a screen of the computing device 115-*d*, the current data corresponding to the monitored physiological parameter.

At 520, the computing device 115-*d* may determine whether there is a medical relationship between the monitored physiological parameter and the health indicator. In a first example, the computing device 115-*d* tray determine that the medical relationship between the monitored physiological parameter and the health indicator is a causal relationship. That is, the computing device 115-*d* may determine that the data represented by the health indicator affects the monitored physiological parameter of the patient. For example, if the health indicator represents that the patient has asthma, the computing device 115-*d* may determine that the asthma affects the monitored physiological parameter (e.g., such as an oxygen saturation level) of the patient. In a second example, the computing device 115-*d* may determine that the data indicated by the health indicator is medically unrelated to the monitored physiological parameter of the patient.

At 525, the computing device 115-*d* may display the health indicator at a second location, where a relationship between the first location and the second location is based on the medical relationship between the monitored physiological parameter and the health indicator. In the example that the relationship between the monitored physiological parameter and the health indicator is a causal relationship, the computing device 115-*d* may arrange the first location on the screen and the second location on the screen within a threshold distance based on the causal relationship. In the example that the monitored physiological parameter is unrelated to the monitored physiological parameter of the patient, the computing device 115-*d* may arrange the first location on the screen and the second location on the screen above a threshold distance. In some cases, the health indicator may be displayed on a separate page from the current data corresponding to the monitored physiological parameter. The computing device 115-*d* may filter the health indicator and one or more additional health indicators by a category to display a subset of the health indicator and the one or more additional health indicators on the monitor.

Figure 6:
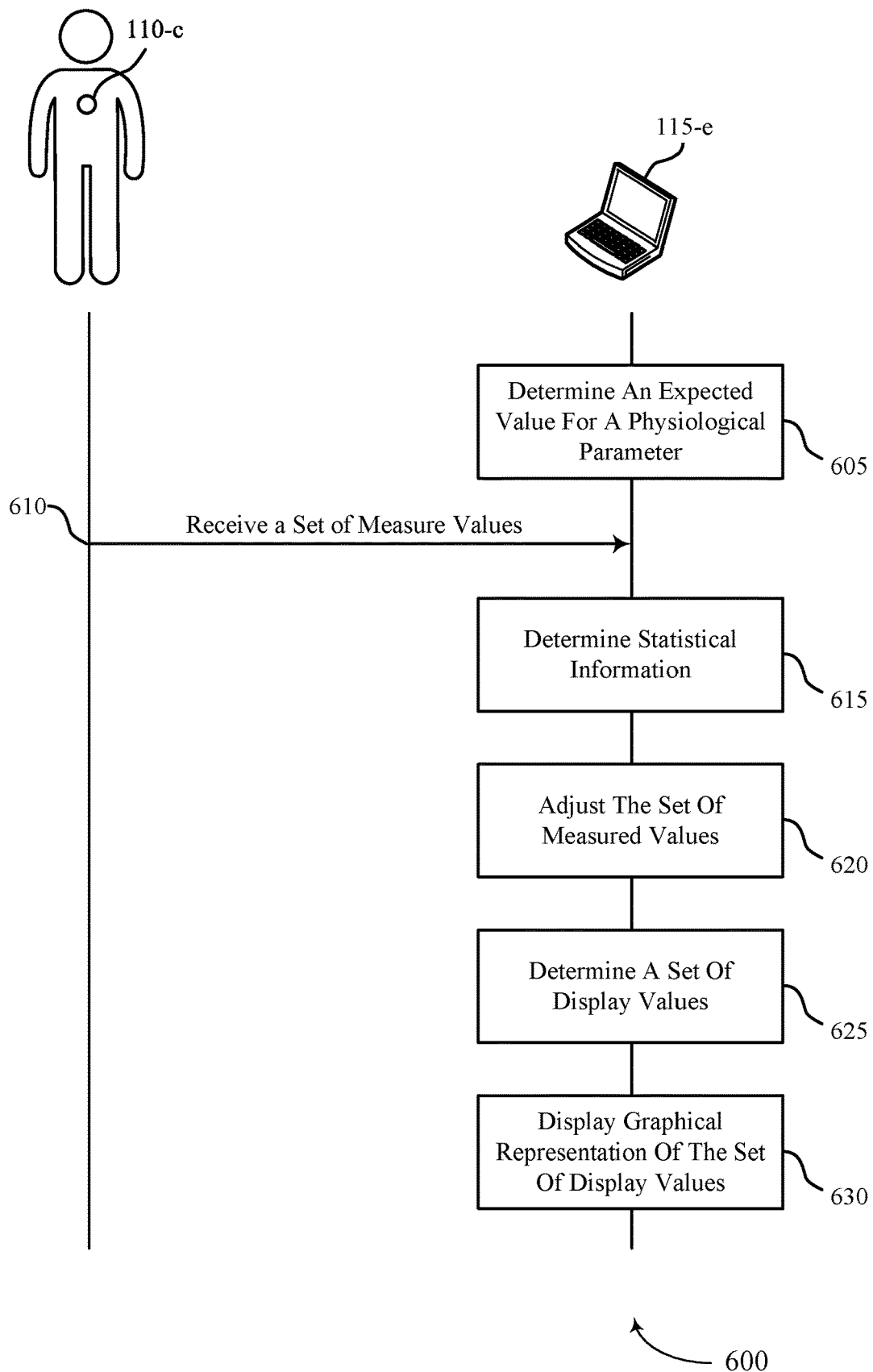

FIG. 6 illustrates an example of a process flow 600 that supports contextual patient data representation and display in accordance with aspects of the present disclosure. Process flow 600 may include computing device 115-*e* and medical device 110-*c*, which may be respective examples of computing device 115 and medical device 110 as described with reference to FIGS. 1-2 and 5. The computing device 115-*e* may be an example of a central station or a monitor as described herein. Alternative examples of the following may be implemented, where some steps are performed in a different order or not at all. Some steps may additionally include features not mentioned above.

At 605, the computing device 115-e may determine an expected value for a physiological parameter of a patient based on a health record of the patient.

At 610, the computing device 115-e may receive, over a period of time, a set of measured values of the physiologic parameter, the set of measured values based on monitoring the physiological parameter of the patient.

At 615, the computing device 115-e may determine statistical information corresponding to the set of measured values over the period of time. In some cases, determining the statistical information may include the computing device 115-e determining a standard deviation of the set of measured values of the period of time and determining a set of demarcation points based on a function of the standard deviation (e.g., half of the standard deviation, a quarter of the standard deviation).

At 620, the computing device 115-e may adjust the set of measured values to a set of adjusted values based on the determined statistical information. In some instances, the set of adjusted values are based on the set of demarcation points (e.g., as determined at 615). For example, the computing device 115-e may round each value of the set of measured values to a nearest value within the set of demarcation points.

At 625, the computing device 115-e may determine a set of display values by selecting a subset of the set of adjusted values. For example, the set of display values may include a temporally first value from the set of adjusted values, a temporally middle value from the set of adjusted values, and a temporally last value from the set of adjusted values. In some other examples, the set of display values may include one or more extrema from the set of adjusted values. In some cases, the set of display values may represent the set of measured values.

At 630, the computing device 115-e may display a graphical representation of the set of display values in relation to the expected value of the physiological parameter. In some cases, the computing device 115-e may display each display value (e.g., from the set of display values as determined at 625) according to a temporal order of the corresponding measured values. This may allow a health care provider to determine the trend of the physiological parameter over time.

Figure 7:
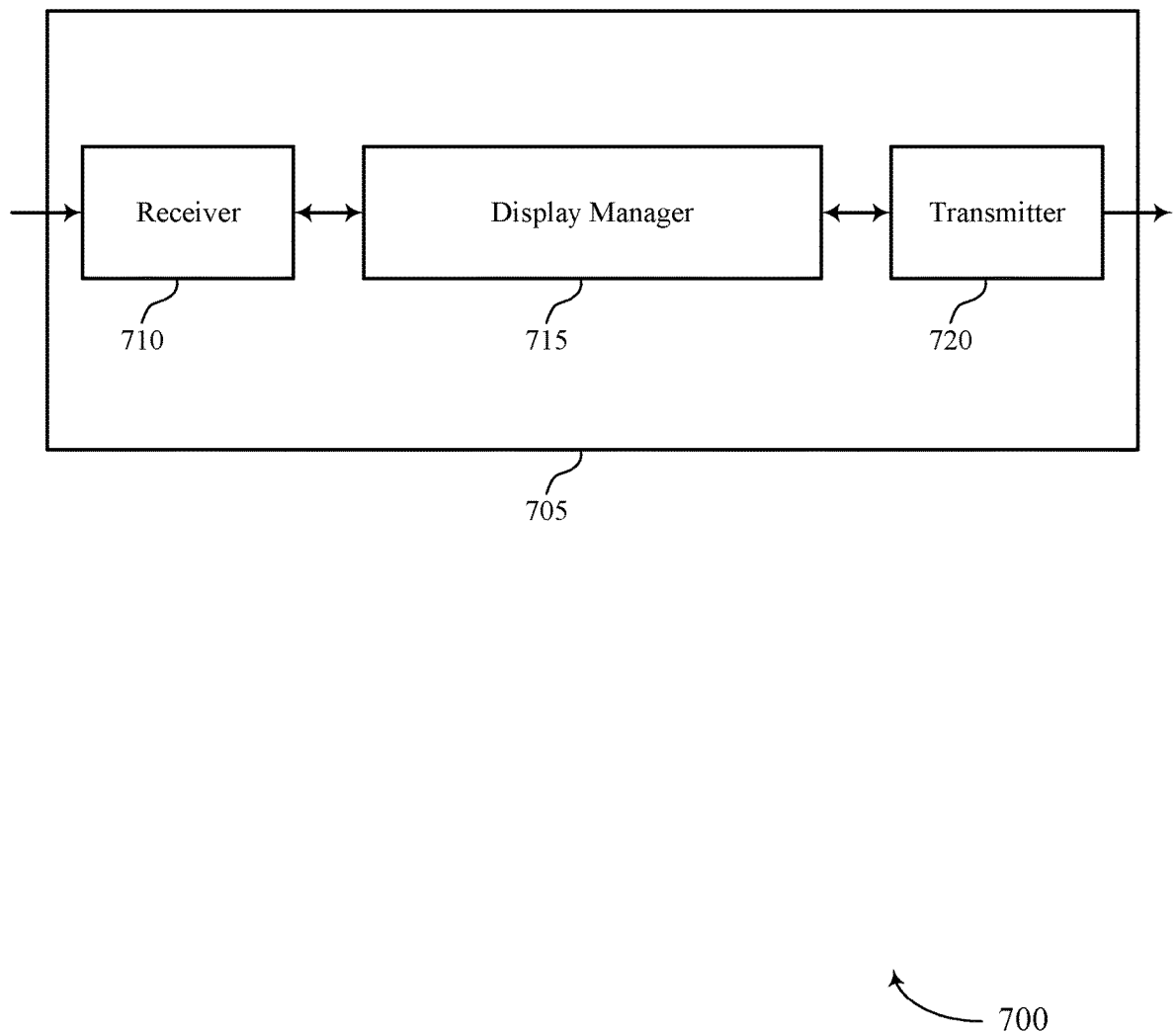
FIGS. 7 and 8 show block diagrams of devices that support contextual patient data representation and display in accordance with aspects of the present disclosure.

FIG. 7 shows a block diagram 700 of a device 705 that supports contextual patient data representation and display in accordance with aspects of the present disclosure. The device 705 may be an example of aspects of a device as described herein. The device 705 may include a receiver 710, a display manager 715, and a transmitter 720. The device 705 may also include a processor. Each of these components may be in communication with one another (e.g., via one or more buses).

The receiver 710 may receive information such as packets, user data, or control information associated with various information channels (e.g., control channels, data channels, and information related to contextual patient data representation and display, etc.). Information may be passed on to other components of the device 705. The receiver 710 may be an example of aspects of the transceiver 1020 described with reference to FIG. 10. The receiver 710 may utilize a single antenna or a set of antennas.

The display manager 715 may determine, at a monitor of a patient, a health indicator for visually representing data related to a health record of the patient, receive, after determining the health indicator, current data corresponding to a monitored physiological parameter, display, at a first location on a screen of the monitor, the current data corresponding to the monitored physiological parameter, determine whether there is a medical relationship between the monitored physiological parameter and the health indicator, and display the health indicator at a second location on the screen, where a relationship between the first location and the second location is based on the medical relationship between the monitored physiological parameter and the health indicator.

The display manager 715 may also determine an expected value for a physiological parameter of a patient based on a health record of the patient, receive, over a period of time, a set of measured values of the physiological parameter, the set of measured values based on monitoring the physiological parameter of the patient, determine statistical information corresponding to the set of measured values over the period of time, adjust the set of measured values to a set of adjusted values based on the determined statistical information, determine a set of display values by selecting a subset of the set of adjusted values, the set of display values representing the set of measured values, and display a graphical representation of the set of display values in relation to the expected value of the physiological parameter. The display manager 715 may be an example of aspects of the display manager 1010 described herein.

The display manager 715, or its sub-components, may be implemented in hardware, code (e.g., software or firmware) executed by a processor, or any combination thereof. If implemented in code executed by a processor, the functions of the display manager 715, or its sub-components may be executed by a general-purpose processor, a DSP, an application-specific integrated circuit (ASIC), a FPGA or other programmable logic device, discrete gate or transistor logic, discrete hardware components, or any combination thereof designed to perform the functions described in the present disclosure.

The display manager 715, or its sub-components, may be physically located at various positions, including being distributed such that portions of functions are implemented at different physical locations by one or more physical components. In some examples, the display manager 715, or its sub-components, may be a separate and distinct component in accordance with various aspects of the present disclosure. In some examples, the display manager 715, or its sub-components, may be combined with one or more other hardware components, including but not limited to an input/output (I/O) component, a transceiver, a network server, another computing device, one or more other components described in the present disclosure, or a combination thereof in accordance with various aspects of the present disclosure.

The transmitter 720 may transmit signals generated by other components of the device 705. In some examples, the transmitter 720 may be collocated with a receiver 710 in a transceiver module. For example, the transmitter 720 may be an example of aspects of the transceiver 1020 described with reference to FIG. 10. The transmitter 720 may utilize a single antenna or a set of antennas.

Figure 8:
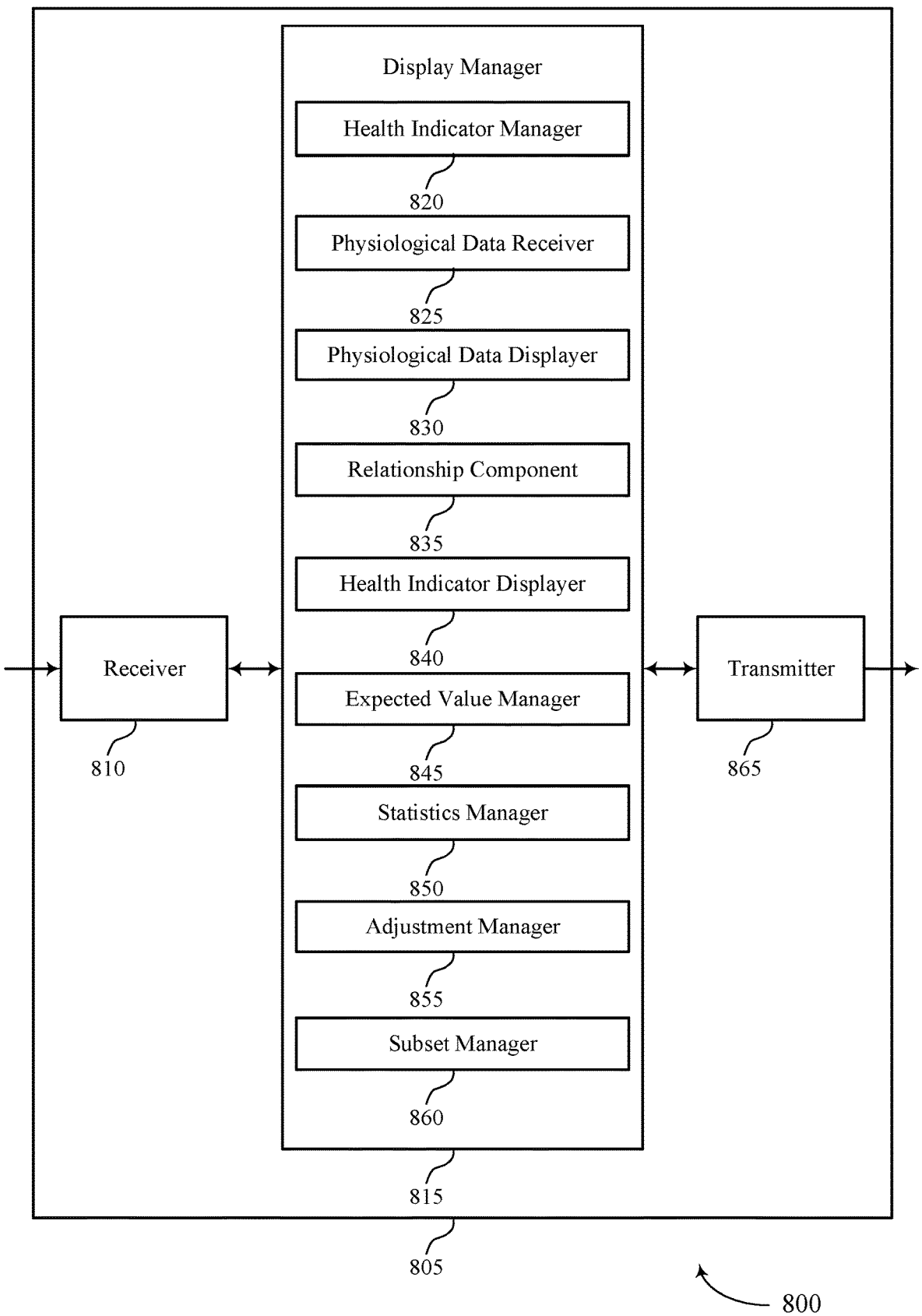

FIG. 8 shows a block diagram 800 of a device 805 that supports contextual patient data representation and display in accordance with aspects of the present disclosure. The device 805 may be an example of aspects of a device 705 or a device 115 as described herein. The device 805 may include a receiver 810, a display manager 815, and a transmitter 865. The device 805 may also include a processor. Each of these components may be in communication with one another (e.g., via one or more buses).

The receiver 810 may receive information such as packets, user data, or control information associated with various information channels (e.g., control channels, data channels, and information related to contextual patient data representation and display, etc.). Information may be passed on to other components of the device 805. The receiver 810 may be an example of aspects of the transceiver 1020 described with reference to FIG. 10. The receiver 810 may utilize a single antenna or a set of antennas.

The display manager 815 may be an example of aspects of the display manager 715 as described herein. The display manager 815 may include a health indicator manager 820, a physiological data receiver 825, a physiological data displayer 830, a relationship component 835, a health indicator displayer 840, an expected value manager 845, a statistics manager 850, an adjustment manager 855, and a subset manager 860. The display manager 815 may be an example of aspects of the display manager 1010 described herein.

The health indicator manager 820 may determine, at a monitor of a patient, a health indicator for visually representing data related to a health record of the patient. The physiological data receiver 825 may receive, after determining the health indicator, current data corresponding to a monitored physiological parameter. The physiological data displayer 830 may display, at a first location on a screen of the monitor, the current data corresponding to the monitored physiological parameter. The relationship component 835 may determine whether there is a medical relationship between the monitored physiological parameter and the health indicator. The health indicator displayer 840 may display the health indicator at a second location on the screen, where a relationship between the first location and the second location is based on the medical relationship between the monitored physiological parameter and the health indicator.

The expected value manager 845 may determine an expected value for a physiological parameter of a patient based on a health record of the patient. The physiological data receiver 825 may receive, over a period of time, a set of measured values of the physiological parameter, the set of measured values based on monitoring the physiological parameter of the patient. The statistics manager 850 may determine statistical information corresponding to the set of measured values over the period of time. The adjustment manager 855 may adjust the set of measured values to a set of adjusted values based on the determined statistical information. The subset manager 860 may determine a set of display values by selecting a subset of the set of adjusted values, the set of display values representing the set of measured values. The physiological data displayer 830 may display a graphical representation of the set of display values in relation to the expected value of the physiological parameter.

The transmitter 865 may transmit signals generated by other components of the device 805. In some examples, the transmitter 865 may be collocated with a receiver 810 in a, transceiver module. For example, the transmitter 865 may be an example of aspects of the transceiver 1020 described with reference to FIG. 10. The transmitter 865 may utilize a single antenna or a set of antennas.

Figure 9:
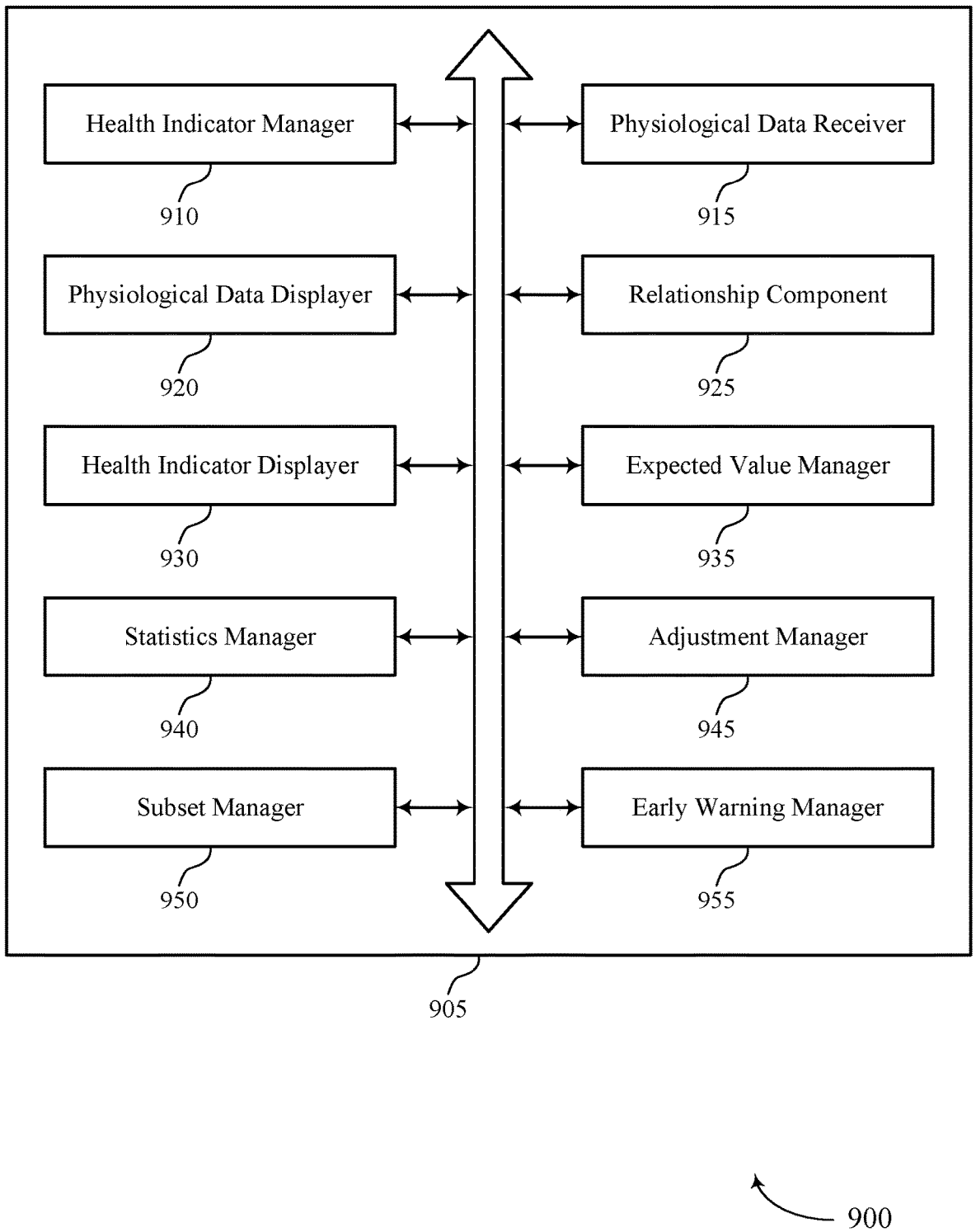
FIG. 9 shows a block diagram of a display manager that supports contextual patient data representation and display in accordance with aspects of the present disclosure.

FIG. 9 shows a block diagram 900 of a display manager 905 that supports contextual patient data representation and display in accordance with aspects of the present disclosure. The display manager 905 may be an example of aspects of a display manager 715, a display manager 815, or a display manager 1010 described herein. The display manager 905 may include a health indicator manager 910, a physiological data receiver 915, a physiological data displayer 920, a relationship component 925, a health indicator displayer 930, an expected value manager 935, a statistics manager 940, an adjustment manager 945, a subset manager 950, and an early warning manager 955. Each of these modules may communicate, directly or indirectly, with one another (e.g., via one or more buses).

The health indicator manager 910 may determine, at a monitor of a patient, a health indicator for visually representing data related to a health record of the patient. The data represented by the health indicator may correspond to a patient condition, a risk factor for the patient, a current medication of the patient, or a combination thereof. In some cases, the health indicator includes an icon indicating the data related to the health record of the patient and a suggested health action based on the data related to the health record. In some examples, the health indicator manager 910 may arrange the first location on the screen and the second location on the screen within a threshold distance based on the causal relationship. In some cases, the health indicator manager 910 may filter the health indicator and one or more additional health indicators by a category to display a subset of the health indicator and the one or more additional health indicators on the monitor.

The physiological data receiver 915 may receive, after determining the health indicator, current data corresponding to a monitored physiological parameter.

The physiological data displayer 920 may display, at a first location on a screen of the monitor, the current data corresponding to the monitored physiological parameter. In some examples, the physiological data displayer 920 may display the current data corresponding to the monitored physiological parameter on a separate page from the health indicator.

The relationship component 925 may determine whether there is a medical relationship between the monitored physiological parameter and the health indicator. In some examples, the relationship component 925 may determine that the medical relationship between the monitored physiological parameter and the health indicator is a causal relationship, where the data represented by the health indicator affects the monitored physiological parameter of the patient. In some examples, the relationship component 925 may determine that data indicated by the health indicator is medically unrelated to the monitored physiological parameter of the patient.

The health indicator displayer 930 may display the health indicator at a second location on the screen, where a relationship between the first location and the second location is based on the medical relationship between the monitored physiological parameter and the health indicator. In some examples, the health indicator displayer 930 may arrange the first location on the screen and the second location on the screen above a threshold distance.

The physiological data receiver 915 may receive, over a period of time, a set of measured values of the physiological parameter, the set of measured values based on monitoring the physiological parameter of the patient.

In some examples, the physiological data displayer 920 may display a graphical representation of the set of display values in relation to the expected value of the physiological parameter. In some examples, the physiological data displayer 920 may display each display value of the set of display values according to a temporal order of the corresponding measured values.

The expected value manager 935 may determine an expected value for a physiological parameter of a patient based on a health record of the patient.

The statistics manager 940 may determine statistical information corresponding to the set of measured values over the period of time. In some examples, the statistics manager 940 may determine a standard deviation of the set of measured values over the period of time. In some examples, the statistics manager 940 may determine a set of demarcation points based on a function of the standard deviation, where the set of adjusted values is based on the set of demarcation points. In some cases, the statistics manager 940 may determine a median value of the set of adjusted values, where the set of display values is the median value. In some instances, the statistics manager 940 may determine a first difference between the median value and a maximum value of the set of adjusted values. In some examples, determining a second difference between the median value and a minimum value of the set of adjusted values, where displaying the graphical representation of the set of display values includes displaying the median value with a first error bar corresponding to the first difference and second error bar corresponding to the second difference.

The adjustment manager 945 may adjust the set of measured values to a set of adjusted values based on the determined statistical information. In some examples, the adjustment manager 945 may round each value of the set of measured values to a nearest value within the set of demarcation points.

The subset manager 950 may determine a set of display values by selecting a subset of the set of adjusted values, the set of display values representing the set of measured values. In some cases, the set of display values includes a temporally first value from the set of adjusted values, a temporally middle value from the set of adjusted values, and a temporally last value from the set of adjusted values. In some examples, the set of display values includes one or more extrema from the set of adjusted values.

The early warning manager 955 may calculate a predicted future value for the physiological parameter by inputting the set of measured values into an early warning function. In some examples, the early warning manager 955 may generate a warning indicating a potential health threat based on the predicted future value.

Figure 10:
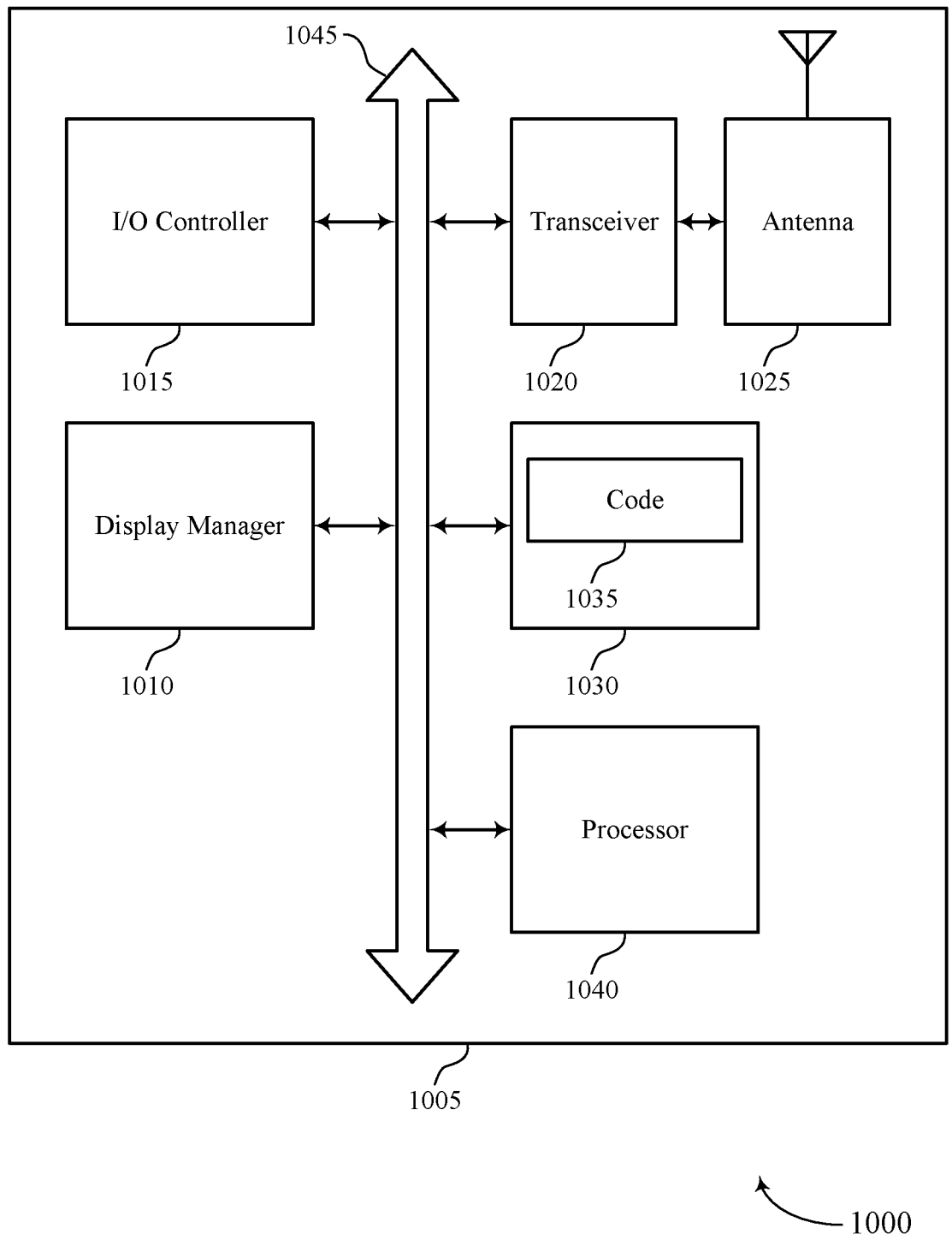
FIG. 10 shows a diagram of a system including a device that supports contextual patient data representation and display in accordance with aspects of the present disclosure.

FIG. 10 shows a diagram of a system 1000 including a device 1005 that supports contextual patient data representation and display in accordance with aspects of the present disclosure. The device 1005 may be an example of or include the components of device 705, device 805, or a device as described herein. The device 1005 may include components for bi-directional voice and data communications including components for transmitting and receiving communications, including a display manager 1010, an I/O controller 1015, a transceiver 1020, an antenna 1025, memory 1030, and a processor 1040. These components may be in electronic communication via one or more buses (e.g., bus 1045).

The display manager 1010 may determine, at a monitor of a patient, a health indicator for visually representing data related to a health record of the patient, receive, after determining the health indicator, current data corresponding to a monitored physiological parameter, display, at a first location on a screen of the monitor, the current data corresponding to the monitored physiological parameter, determine whether there is a medical relationship between the monitored physiological parameter and the health indicator, and display the health indicator at a second location on the screen, where a relationship between the first location and the second location is based on the medical relationship between the monitored physiological parameter and the health indicator.

The display manager 1010 may also determine an expected value for a physiological parameter of a patient based on a health record of the patient, receive, over a period of time, a set of measured values of the physiological parameter, the set of measured values based on monitoring the physiological parameter of the patient, determine statistical information corresponding to the set of measured values over the period of time, adjust the set of measured values to a set of adjusted values based on the determined statistical information, determine a set of display values by selecting a subset of the set of adjusted values, the set of display values representing the set of measured values, and display a graphical representation of the set of display values in relation to the expected value of the physiological parameter.

The I/O controller 1015 may manage input and output signals for the device 1005. The I/O controller 1015 may also manage peripherals not integrated into the device 1005. In some cases, the I/O controller 1015 may represent a physical connection or port to an external peripheral. In some cases, the I/O controller 1015 may utilize an operating system such as iOS®, ANDROID®, MS-DOS®, MS-WINDOWS®, OS/2®, UNIX®, LINUX®, or another known operating system. In other cases, the I/O controller 1015 may represent or interact with a modem, a keyboard, a mouse, a touchscreen, or a similar device. In some cases, the I/O controller 1015 may be implemented as part of a processor. In some cases, a user may interact with the device 1005 via the I/O controller 1015 or via hardware components controlled by the I/O controller 1015.

The transceiver 1020 may communicate bi-directionally, via one or more antennas, wired, or wireless links as described herein. For example, the transceiver 1020 may represent a wireless transceiver and may communicate bi-directionally with another wireless transceiver. The transceiver 1020 may also include a modem to modulate the packets and provide the modulated packets to the antennas for transmission, and to demodulate packets received from the antennas.

In some cases, the wireless device may include a single antenna 1025. However, in some cases the device may have more than one antenna 1025, which may be capable of concurrently transmitting or receiving multiple wireless transmissions.

The memory 1030 may include RAM and ROM. The memory 1030 may store computer-readable, computer-executable code 1035 including instructions that, when executed, cause the processor to perform various functions described herein. In some cases, the memory 1030 may contain, among other things, a BIOS which may control basic hardware or software operation such as the interaction with peripheral components or devices.

The processor 1040 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 1040 may be configured to operate a memory array using a memory controller. In other cases, a memory controller may be integrated into the processor 1040. The processor 1040 may he configured to execute computer-readable instructions stored in a memory (e.g., the memory 1030) to cause the device 1005 to perform various functions (e.g., functions or tasks supporting contextual patient data representation and display).

The code 1035 may include instructions to implement aspects of the present disclosure, including instructions to support patient monitoring. The code 1035 may be stored in a non-transitory computer-readable medium such as system memory or other type of memory. In some cases, the code 1035 may not be directly executable by the processor 1040 but may cause a computer (e.g., when compiled and executed) to perform functions described herein.

Figure 11:
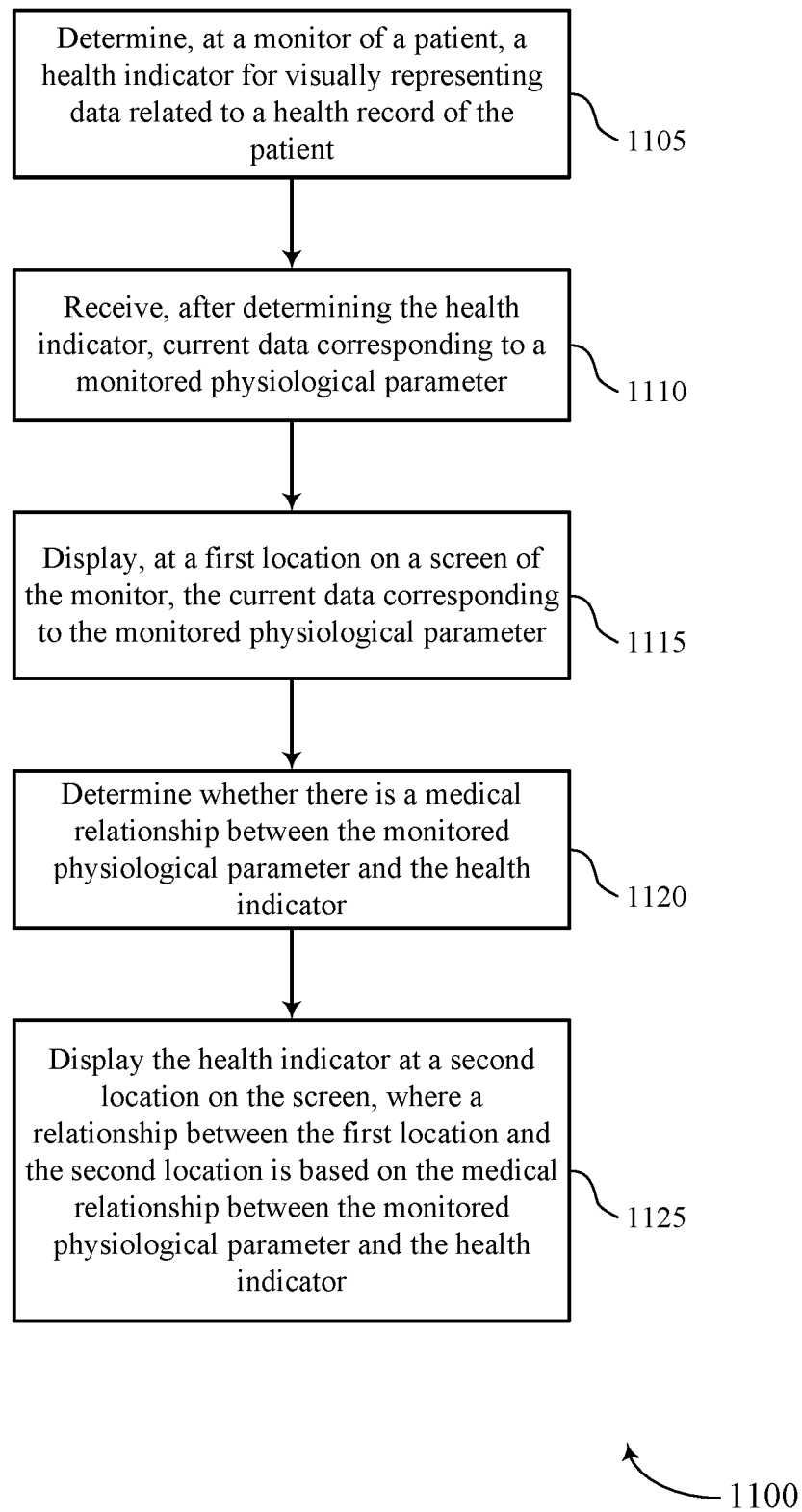
FIGS. 11 through 14 show flowcharts illustrating methods that support contextual patient data representation and display in accordance with aspects of the present disclosure.

FIG. 11 shows a flowchart illustrating a method 1100 that supports contextual patient data representation and display in accordance with aspects of the present disclosure. The operations of method 1100 may be implemented by a device or its components as described herein. For example, the operations of method 1100 may be performed by a display manager as described with reference to FIGS. 7 through 10. In some examples, a device may execute a set of instructions to control the functional elements of the device to perform the functions described herein. Additionally or alternatively, a device may perform aspects of the functions described herein using special-purpose hardware.

At 1105, the device may determine, at a monitor of a patient, a health indicator for visually representing data related to a health record of the patient. The operations of 1105 may be performed according to the methods described herein. In some examples, aspects of the operations of 1105 may he performed by a health indicator manager as described with reference to FIGS. 7 through 10.

At 1110, the device may receive, after determining the health indicator, current data corresponding to a monitored physiological parameter. The operations of 1110 may be performed according to the methods described herein. In some examples, aspects of the operations of 1110 may be performed by a physiological data receiver as described with reference to FIGS. 7 through 10.

At 1115, the device may display, at a first location on a screen of the monitor, the current data corresponding to the monitored physiological parameter. The operations of 1115 may be performed according to the methods described herein. In some examples, aspects of the operations of 1115 may be performed by a physiological data displayer as described with reference to FIGS. 7 through 10.

At 1120, the device may determine whether there is a medical relationship between the monitored physiological parameter and the health indicator. The operations of 1120 may he performed according to the methods described herein. In some examples, aspects of the operations of 1120 may be performed by a relationship component as described with reference to FIGS. 7 through 10.

At 1125, the device may display the health indicator at a second location on the screen, where a relationship between the first location and the second location is based on the medical relationship between the monitored physiological parameter and the health indicator. The operations of 1125 may he performed according to the methods described herein. In some examples, aspects of the operations of 1125 may be performed by a health indicator displayer as described with reference to FIGS. 7 through 10.

Figure 12:
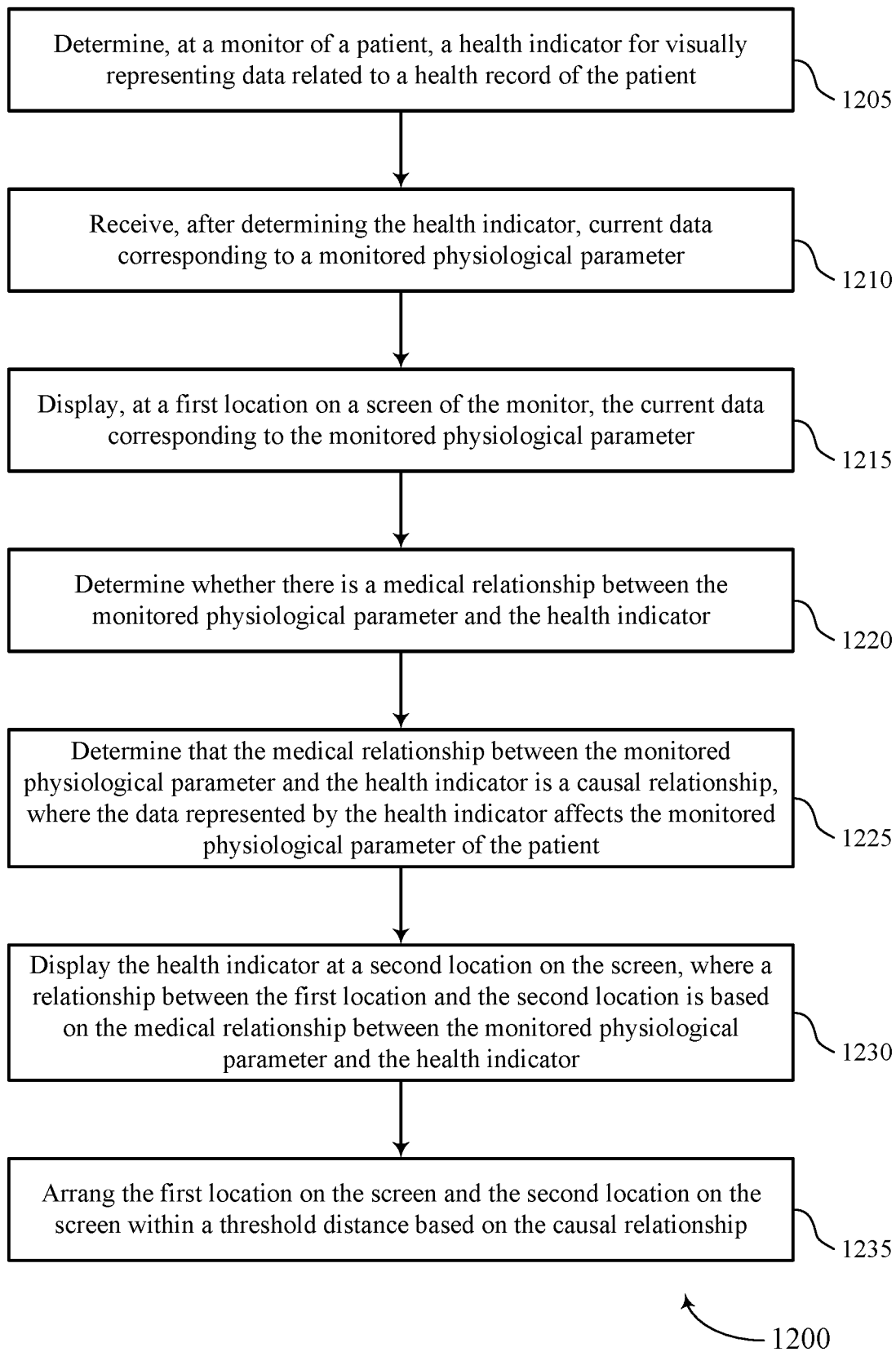

FIG. 12 shows a flowchart illustrating a method 1200 that supports contextual patient data representation and display in accordance with aspects of the present disclosure. The operations of method 1200 may be implemented by a device or its components as described herein. For example, the operations of method 1200 may be performed by a display manager as described with reference to FIGS. 7 through 10. In some examples, a device may execute a set of instructions to control the functional elements of the device to perform the functions described herein. Additionally or alternatively, a device may perform aspects of the functions described herein using special-purpose hardware.

At 1205, the device may determine, at a monitor of a patient, a health indicator for visually representing data related to a health record of the patient. The operations of 1205 may be performed according to the methods described herein. In some examples, aspects of the operations of 1205 may be performed by a health indicator manager as described with reference to FIGS. 7 through 10.

At 1210, the device may receive, after determining the health indicator, current data corresponding to a monitored physiological parameter. The operations of 1210 may be performed according to the methods described herein. In some examples, aspects of the operations of 1210 may be performed by a physiological data receiver as described with reference to FIGS. 7 through 10.

At 1215, the device may display, at a first location on a screen of the monitor, the current data corresponding to the monitored physiological parameter. The operations of 1215 may be performed according to the methods described herein. In some examples, aspects of the operations of 1215 may be performed by a physiological data displayer as described with reference to FIGS. 7 through 10.

At 1220, the device may determine whether there is a medical relationship between the monitored physiological parameter and the health indicator. The operations of 1220 may be performed according to the methods described herein. In some examples, aspects of the operations of 1220 may be performed by a relationship component as described with reference to FIGS. 7 through 10.

At 1225, the device may determine that the medical relationship between the monitored physiological parameter and the health indicator is a causal relationship, where the data represented by the health indicator affects the monitored physiological parameter of the patient. The operations of 1225 may be performed according to the methods described herein. In some examples, aspects of the operations of 1225 may be performed by a relationship component as described with reference to FIGS. 7 through 10.

At 1230, the device may display the health indicator at a second location on the screen, where a relationship between the first location and the second location is based on the medical relationship between the monitored physiological parameter and the health indicator. The operations of 1230 may be performed according to the methods described herein. In some examples, aspects of the operations of 1230 may be performed by a health indicator displayer as described with reference to FIGS. 7 through 10.

At 1235, the device may arrange the first location on the screen and the second location on the screen within a threshold distance based on the causal relationship. The operations of 1235 may be performed according to the methods described herein. In some examples, aspects of the operations of 1235 may be performed by a health indicator manager as described with reference to FIGS. 7 through 10.

Figure 13:
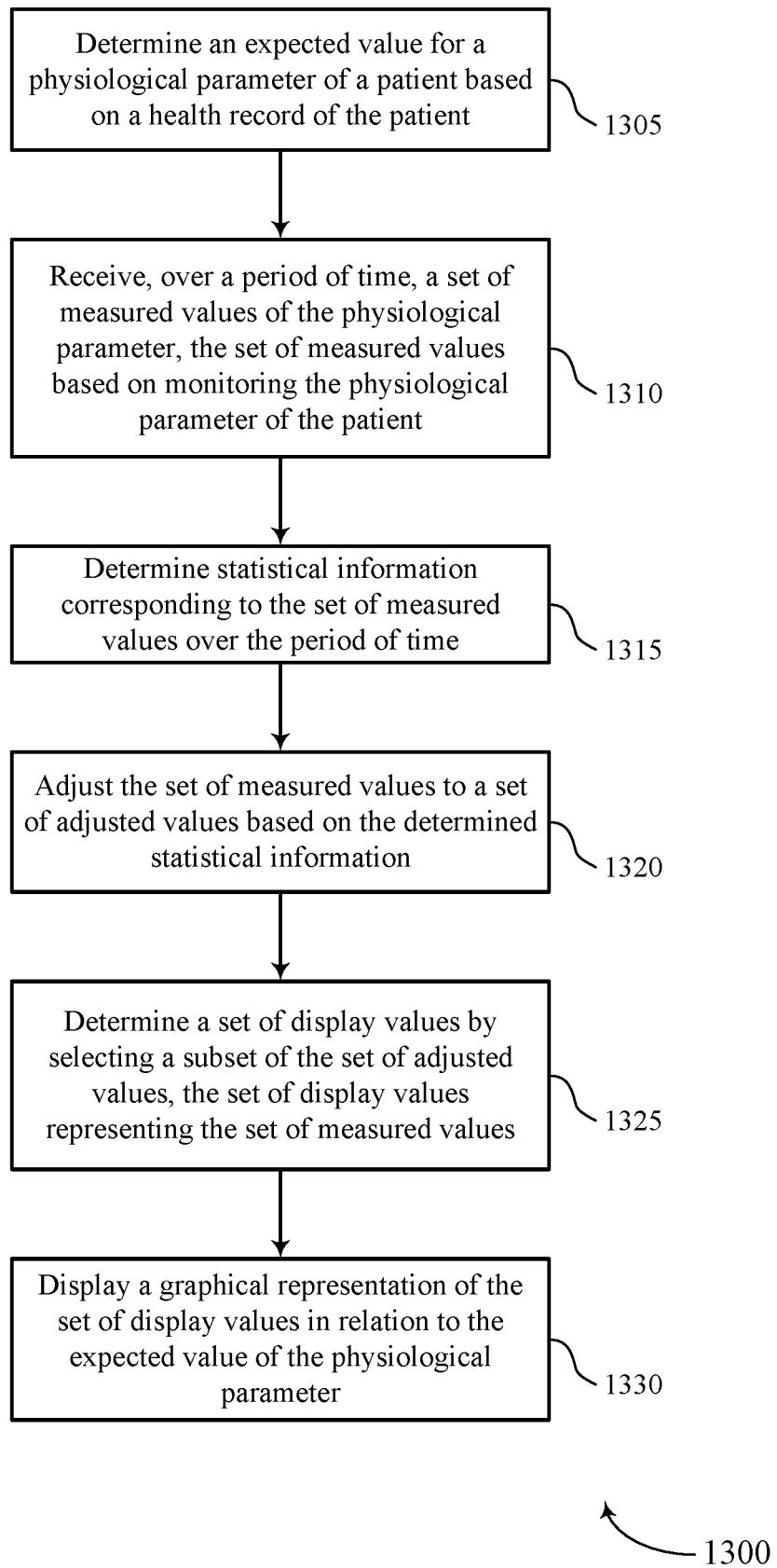

FIG. 13 shows a flowchart illustrating a method 1300 that supports contextual patient data representation and display in accordance with aspects of the present disclosure. The operations of method 1300 may he implemented by a device or its components as described herein. For example, the operations of method 1300 may be performed by a display manager as described with reference to FIGS. 7 through 10. In some examples, a device may execute a set of instructions to control the functional elements of the device to perform the functions described herein. Additionally or alternatively, a device may perform aspects of the functions described herein using special-purpose hardware.

At 1305, the device may determine an expected value for a physiological parameter of a patient based on a health record of the patient. The operations of 1305 may be performed according to the methods described herein. In some examples, aspects of the operations of 1305 may be performed by an expected value manager as described with reference to Ms. 7 through 10.

At 1310, the device may receive, over a period of time, a set of measured values of the physiological parameter, the set of measured values based on monitoring the physiological parameter of the patient. The operations of 1310 may be performed according to the methods described herein. In some examples, aspects of the operations of 1310 may be performed by a physiological data receiver as described with reference to FIGS. 7 through 10.

At 1315, the device may determine statistical information corresponding to the set of measured values over the period of time. The operations of 1315 may be performed according to the methods described herein. In some examples, aspects of the operations of 1315 may be performed by a statistics manager as described with reference to FIGS. 7 through 10.

At 1320, the device may adjust the set of measured values to a set of adjusted values based on the determined statistical information. The operations of 1320 may be performed according to the methods described herein. In some examples, aspects of the operations of 1320 may be performed by an adjustment manager as described with reference to FIGS. 7 through 10.

At 1325, the device may determine a set of display values by selecting a subset of the set of adjusted values, the set of display values representing the set of measured values. The operations of 1325 may be performed according to the methods described herein. In some examples, aspects of the operations of 1325 may be performed by a subset manager as described with reference to FIGS. 7 through 10.

At 1330, the device may display a graphical representation of the set of display values in relation to the expected value of the physiological parameter. The operations of 1330 may be performed according to the methods described herein. In some examples, aspects of the operations of 1330 may be performed by a physiological data displayer as described with reference to FIGS. 7 through 10.

Figure 14:
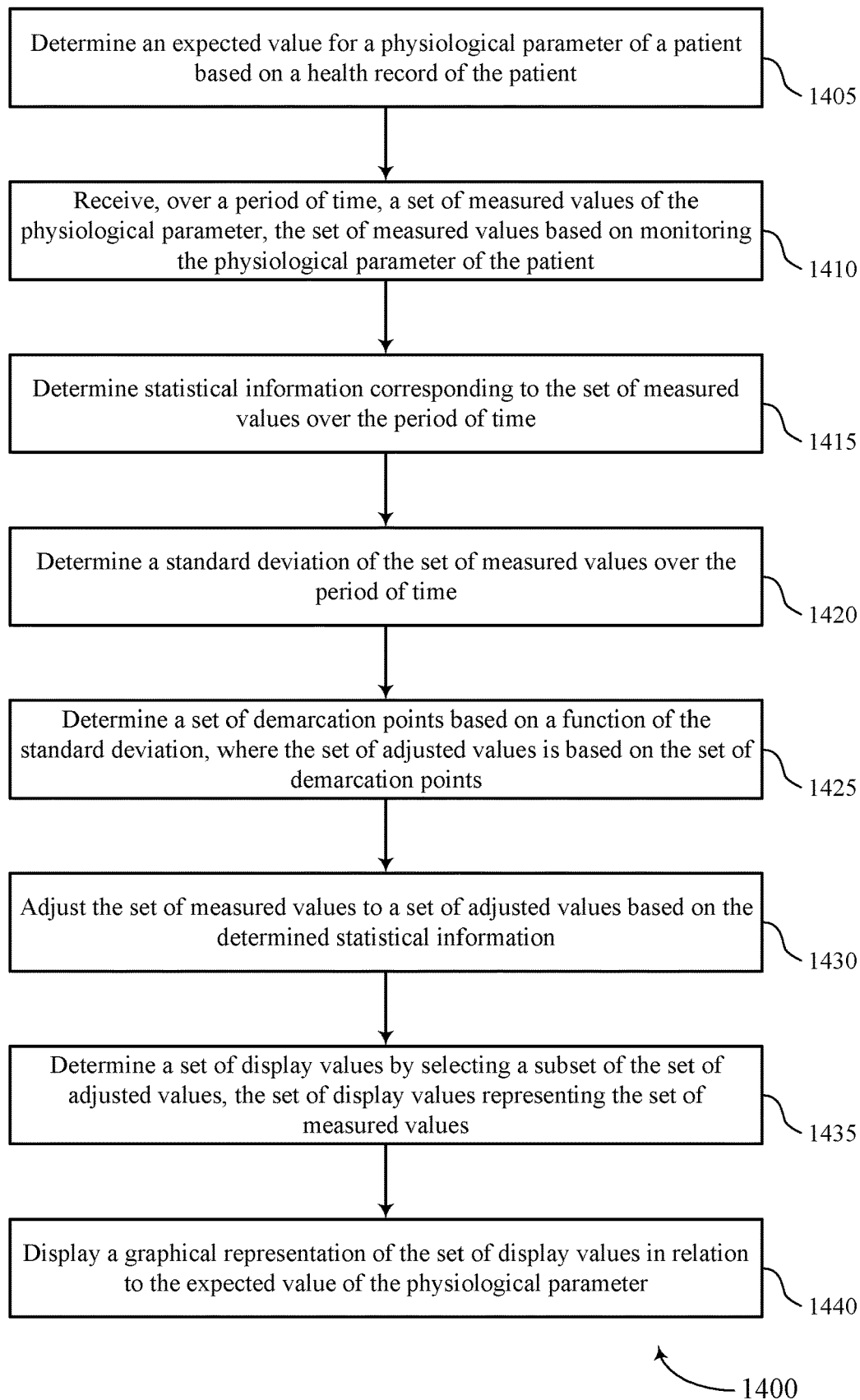

FIG. 14 shows a flowchart illustrating a method 1400 that supports contextual patient data representation and display in accordance with aspects of the present disclosure. The operations of method 1400 may be implemented by a device or its components as described herein. For example, the operations of method 1400 may be performed by a display manager as described with reference to FIGS. 7 through 10. In some examples, a device may execute a set of instructions to control the functional elements of the device to perform the functions described herein. Additionally or alternatively, a device may perform aspects of the functions described herein using special-purpose hardware.

At 1405, the device may determine an expected value for a physiological parameter of a patient based on a health record of the patient. The operations of 1405 may be performed according to the methods described herein. In some examples, aspects of the operations of 1405 may be performed by an expected value manager as described with reference to FIGS. 7 through 10.

At 1410, the device may receive, over a period of time, a set of measured values of the physiological parameter, the set of measured values based on monitoring the physiological parameter of the patient. The operations of 1410 may be performed according to the methods described herein. In some examples, aspects of the operations of 1410 may be performed by a physiological data receiver as described with reference to FIGS. 7 through 10.

At 1415, the device may determine statistical information corresponding to the set of measured values over the period of time. The operations of 1415 may be performed according to the methods described herein. In some examples, aspects of the operations of 1415 may be performed by a statistics manager as described with reference to FIGS. 7 through 10.

At 1420, the device may determine a standard deviation of the set of measured values over the period of time. The operations of 1420 may he performed according to the methods described herein. In some examples, aspects of the operations of 1420 may he performed by a statistics manager as described with reference to FIGS. 7 through 10.

At 1425, the device may determine a set of demarcation points based on a function of the standard deviation, where the set of adjusted values is based on the set of demarcation points. The operations of 1425 may be performed according to the methods described herein. In some examples, aspects of the operations of 1425 may be performed by a statistics manager as described with reference to FIGS. 7 through 10.

At 1430, the device may adjust the set of measured values to a set of adjusted values based on the determined statistical information. The operations of 1430 may be performed according to the methods described herein. In sonic examples, aspects of the operations of 1430 may be performed by an adjustment manager as described with reference to FIGS. 7 through 10.

At 1435, the device may determine a set of display values by selecting a subset of the set of adjusted values, the set of display values representing the set of measured values. The operations of 1435 may be performed according to the methods described herein. In sonic examples, aspects of the operations of 1435 may be performed by a subset manager as described with reference to FIGS. 7 through 10.

At 1440, the device may display a graphical representation of the set of display values in relation to the expected value of the physiological parameter. The operations of 1440 may be performed according to the methods described herein. In some examples, aspects of the operations of 1440 may be performed by a physiological data displayer as described with reference to FIGS. 7 through 10.

It should be noted that the methods described herein describe possible implementations, and that the operations and the steps may be rearranged or otherwise modified and that other implementations are possible. Further, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). A processor may in some cases be in electronic communication with a memory, where the memory stores instructions that are executable by the processor. Thus, the functions described herein may be performed by one or more other processing units (or cores), on at least one integrated circuit (IC). In various examples, different types of ICs may be used (e.g., Structured/Platform ASICs, an FPGA, or another semi-custom IC), which may be programmed in any manner known in the art. The functions of each unit may also be implemented, in whole or in part, with instructions embodied in a memory, formatted to be executed by one or more general or application-specific processors.

The functions described herein may he implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described herein may be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media may comprise RAM, ROM, electrically erasable programmable read only memory (EEPROM), compact disk (CD) ROM or other optical disk storage, magnetic disk storage or other magnetic storage devices, or any other non-transitory medium that may be used to carry or store desired program code means in the form of instructions or data structures and that may be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may he applied to other variations without departing from the scope of the disclosure. Thus, the disclosure is not limited to the examples and designs described herein, but is to be accorded the broadest scope consistent with the principles and novel features disclosed herein.

What is claimed is:

1. A method for patient monitoring, comprising:
   determining, via a processor of a monitor for displaying medical information associated with a patient, a first health indicator icon for visually representing first data related to a health record of the patient and a second health indicator icon for visually representing second data related to the health record of the patient;
   receiving, at the processor, current data corresponding to a monitored physiological parameter from a sensor of a medical device coupled with the patient;
   causing, via the processor, the monitor to display at a first location on a screen of the monitor a visual representation of the current data corresponding to the monitored physiological parameter;
   determining, via the processor, that the first data represented by the first health indicator icon is associated with the monitor physiological parameter based on the first data being related to the current data corresponding to the monitored physiological parameter;
   determining, via the processor, that the second data represented by the second health indicator icon is not associated with the monitored physiological parameter based on the second data being unrelated to the current data corresponding to the monitored physiological parameter;
   in response to determining that the first data is associated with the monitored physiological parameter, causing, via the processor, the monitor to display, the first health indicator icon at a second location on the screen, wherein the second location is at a first distance from the visual representation of the current data corresponding to the monitored physiological parameter, and wherein the first distance indicates that the first data is associated with the monitored physiological parameter; and in response to determining that the second data is not associated with the monitored physiological parameter, causing, via the processor, the monitor to display the second health indicator icon at a third location on the screen, wherein the third location is at a second distance from the visual representation of the current data corresponding to the monitored physiological parameter, and wherein the second distance is greater than the first distance to indicate that the second data is not associated with the monitored physiological parameter.

2. The method of claim 1, wherein determining whether the first data is associated with the monitored physiological parameter further comprises determining, via the processor, whether a first category associated with the first data corresponds with a second category associated with the monitored physiological parameter of the patient.

3. The method of claim 1, wherein the first data represented by the first health indicator icon and the second data represented by the second health indicator icon each correspond to a patient condition, a risk factor for the patient, a current medication of the patient, or a combination thereof.

4. The method of claim 1, further comprising:
displaying the current data corresponding to the monitored physiological parameter on a separate page from the first health indicator icon and the second health indicator icon.

5. The method of claim 1, wherein the first health indicator icon indicates the first data related to the health record of the patient and a suggested health action based on the data related to the health record.

6. The method of claim 1, further comprising:
filtering, by the processor, a set of health indicator icons by a category to determine the first health indicator icon and the second health indicator icon to display on the monitor.

7. An apparatus for patient monitoring, comprising:
a processor,
memory in electronic communication with the processor; and
instructions stored in the memory and executable by the processor to cause the apparatus to:
determine, via the processor, a first health indicator icon for visually representing first data related to a health record of a patient and a second health indicator icon for visually representing second data related to the health record of the patient;
receive, at the processor, current data corresponding to a monitored physiological parameter from a sensor coupled to the patient;
causing, via the processor, a monitor of the apparatus to display, at a first location on a screen of the monitor, a visual representation of the current data corresponding to the monitored physiological parameter;
determine, via the processor, that the first data represented by the first health indicator icon is associated with the monitor physiological parameter based on the first data being related to the current data corresponding to the monitored physiological parameter;

determine, via the processor, that the second data represented by the second health indicator icon is not associated with the monitored physiological parameter based on the second data being unrelated to the current data corresponding to the monitored physiological parameter;

in response to determining that the first data is associated with the monitored physiological parameter, position, via the processor, the first health indicator icon at a second location on the screen, wherein the second location is at a first distance from the visual representation of the current data corresponding to the monitored physiological parameter, and wherein the first distance indicates that the first data is associated with the monitored physiological parameter; and in response to determining that the second data is not associated with the monitored physiological parameters, position, via the processor, the second health indicator icon at a third location on the screen, wherein the third location is at a second distance from the visual representation of the current data corresponding to the monitored physiological parameter; and wherein the second distance is greater than the first distance to indicate that the second data is not associated with the monitored physiological parameter.

8. The apparatus of claim 7, wherein the instructions that are executable by the processor to cause the apparatus to determine whether the first data is associated with the monitored physiological parameter are further executable by the processor to cause the apparatus to:
determine, via the processor, whether a first category associated with the first data corresponds with a second category associated with the monitored physiological parameter of the patient.

9. The apparatus of claim 7, wherein the first data represented by the first health indicator icon and the second data represented by the second health indicator icon each correspond to a patient condition, a risk factor for the patient, a current medication of the patient, or a combination thereof.

10. An apparatus for patient monitoring, comprising:
means for determining a first health indicator icon for visually representing first data related to a health record of a patient and a second health indicator icon for visually representing second data related to the health record of the patient;
means for receiving current data corresponding to a monitored physiological parameter sensed by a medical device coupled with the patient;
means for displaying, at a first location on a screen of a monitor of the apparatus, a visual representation of the current data corresponding to the monitored physiological parameter;
means for determining that the first data represented by the first health indicator icon is associated with the monitor physiological parameter based on the first data being related to the current data corresponding to the monitored physiological parameter;
means for determining that the second data represented by the second health indicator icon is not associated with the monitored physiological parameter based on the second data being unrelated to the current data corresponding to the monitored physiological parameter;
means for displaying the first health indicator icon at a second location on the screen based on determining that the first data is associated with the monitored physiological parameter, wherein the second location is at a first distance from the visual representation of the current data corresponding to the monitored physiological parameter, and wherein the first distance indicates that the first data is associated with the monitored physiological parameter; and means for displaying the second health indicator icon at a third location on the screen based on determining that the second data is not associated with the monitored physiological parameter, wherein the second location is at a second distance from the visual representation of the current data corresponding to the monitored physiological parameter, and wherein the second distance is greater than the first distance to indicate that the second data is not associated with the monitored physiological parameter.

11. The apparatus of claim 10, wherein the means for determining whether the first data is associated with the monitored physiological parameter further comprises means for determining whether a first category associated with the first data represented by the first health indicator icon corresponds with a second category associated with the monitored physiological parameter of the patient.

* * * * *